(12) United States Patent
Gore et al.

(10) Patent No.: US 8,894,975 B2
(45) Date of Patent: Nov. 25, 2014

(54) METHODS OF LEUKEMIA CELL DETECTION

(75) Inventors: Lia Gore, Denver, CO (US); Deborah Deryckere, Boulder, CO (US); Margaret E. Macy, Denver, CO (US); Natalie Serkova, Denver, CO (US)

(73) Assignee: The Regents of the University of Colorado, a body Corporate, Denver, CO (US)

( * ) Notice: Subject to any disclaimer, the term of this patent is extended or adjusted under 35 U.S.C. 154(b) by 0 days.

(21) Appl. No.: 13/264,943

(22) PCT Filed: Apr. 19, 2010

(86) PCT No.: PCT/US2010/031633
§ 371 (c)(1),
(2), (4) Date: Nov. 23, 2011

(87) PCT Pub. No.: WO2010/121263
PCT Pub. Date: Oct. 21, 2010

(65) Prior Publication Data
US 2012/0064009 A1 Mar. 15, 2012

Related U.S. Application Data

(60) Provisional application No. 61/170,512, filed on Apr. 17, 2009.

(51) Int. Cl.
*A61B 5/055* (2006.01)
*A61B 5/00* (2006.01)
*G01R 33/56* (2006.01)

(52) U.S. Cl.
CPC ............... *A61B 5/055* (2013.01); *A61B 5/4504* (2013.01); *G01R 33/56* (2013.01); *A61B 5/416* (2013.01); *Y10S 514/908* (2013.01)
USPC ............................. 424/9.3; 514/908; 435/6.14

(58) Field of Classification Search
CPC ....... A61B 5/055; A61B 5/4505; G01R 33/56
USPC ............................. 424/9.3; 514/908; 435/6.14
See application file for complete search history.

(56) References Cited

U.S. PATENT DOCUMENTS

| | | |
|---|---|---|
| 2003/0170697 A1 | 9/2003 | Goldenberg |
| 2009/0047212 A1 | 2/2009 | Berman et al. |
| 2009/0088578 A1 | 4/2009 | Lascola et al. |

OTHER PUBLICATIONS

Montfoort A et al, Changes in the Cholesterol and Phospholipid Content of Mouse Spleen after Rauscher Leukemia Virus Infection, Lipids 11: 798-801, 1976.*
Xu Z et al, Determination of the Cencentration of Free Fatty Acids in the Plasma of Patients with Malignant Hematopoietic Diseases by Gas Chromatography, Chinese J Chromat 12: 268-269, 1994.*
Griffin & Shockcor "Metabolic Profiles of Cancer Cells." (2004) Nature Reviews: Cancer, vol. 4:551-561.*
International Preliminary Report on Patentability and Written Opinion dated Oct. 18, 2011 for International PCT Application No. PCT/US2010/031633, 5 Pages.
Deberardinis, Ralph J. et al., "The biology of cancer: metabolic reprogramming fuels cell growth and proliferation", Jan. 2008, Cell Metabolism 7:11-20.
Evelhoch, Jeffrey L. et al., "Applications of magnetic resonance in model systems: cancer therapeutics[1] ", Jan.-Apr. 2000, Neoplasia 2(1-2):152-165.
Gerard, Elizabeth L., MD et al., "Compositional changes in vertebral bone marrow during treatment for acute leukemia: assessment with quantitative chemical shift imaging", Radiology, Apr. 1992, 183(1):39-46.
Glunde, Kristine et al., "Therapeutic targets and biomarkers identified in cancer choline phospholipid metabolism", Pharmacogenomics (2006) 7(7):1109-1123.
Gottschalk, Sven et al., "Imatinib (STI57I)—mediated changes in glucose metabolism in human leukemia BCR-ABL-positive cells", Oct. 1, 2004, Clinical Cancer Research 10:6661-6668.
International Search Report dated Nov. 1, 2010 for International Application No. PCT/US2010/031633, 3 pages.
Moulopoulos, Lia A. et al., "Magnetic resonance imaging of the bone marrow in hematologic malignancies", Blood, Sep. 15, 1997, 90(6):2127-2147.
Spratlin, Jennifer L. et al., "Clinical applications of metabolomics in oncology: a review", Jan. 15, 2009, Clinical Cancer Research 15:431-440.
Steelman, L.S. et al., "Contributions of the Raf/MEK/ERK, P13K/PTEN/Akt/mTOR and Jak/STAT pathways to leukemia", 2008, Leukemia 22:686-707.

* cited by examiner

*Primary Examiner* — Jon P Weber
*Assistant Examiner* — Teresa E Knight
(74) *Attorney, Agent, or Firm* — Kilpatrick Townsend & Stockton LLP

(57) ABSTRACT

Methods are provided for, inter alia, determining the presence of leukemia cells in a subject, determining the change or potential change in the number of leukemia cells in the subject with time, determining whether a tissue in a subject contains a plurality of leukemia cells or a plurality progenitor leukemia cells, and determining whether a leukemia therapy administered to a subject is capable of decreasing the number of leukemia cells in a tissue of the subject.

10 Claims, 8 Drawing Sheets

Wild-Type

MLL-AF9 Tg

METHODS OF LEUKEMIA CELL DETECTION

CROSS-REFERENCES TO RELATED APPLICATIONS

This application is a National Stage application of PCT/US2010/031633, filed Apr. 19, 2010, and claims the benefit of U.S. Provisional Application No. 61/170,512, filed Apr. 17, 2009, which is incorporated herein by reference in its entirety and for all purposes.

BACKGROUND OF THE INVENTION

Leukemia is the most common malignancy in childhood, accounting for more than 3000 new diagnoses in the U.S. each year. See *Cancer Statistics Branch NCI. Cancer Incidence and Survival among Children and Adolescents: United States SEER Program*, 1975-1995, 1999. Over 90% of these are acute leukemias of lymphoid or myeloid origin.

Standard methods for assessing treatment response in patients with leukemia have historically relied on repeat sampling of bone marrow and measurement of tumor burden using histopathologic and molecular approaches. These methods assess tumor regression or stabilization and, thus, do not provide evidence of early biochemical or cellular responses to therapy. For molecularly-targeted therapies, biochemical changes in the known target(s) are often assessed in an effort to identify more dynamic indicators of efficacy. However, in many cases, expression and/or activity of the presumed target(s) does not correlate with tumor response (Hamilton et al., 2005, *J Clin Oncol*. 23:6107-6116; Kelly et al., 2005, *J Clin Oncol*. 23:3923-3931; Di Maio et al., 2005, *J Cell Physiol*. 205:355-363), and the relevant therapeutic target is not known. Thus, the identification and validation of additional dynamic biomarkers that are accurate predictors of therapeutic efficacy allow for earlier determination of clinical response and thereby facilitate decreased exposure to ineffective and potentially toxic therapies and are useful to expedient conversion to more effective therapies when there is a poor response.

Novel non-invasive markers of leukemia assessed at diagnosis have prognostic value allowing for identification of patients in need of more intensive therapy. For example without limitation, such non-invasive markers of leukemia are desirable for early detection and staging of pediatric acute lymphoblastic leukemia (ALL) and are crucial for routine longitudinal assessment of therapy response. Thus, development of additional indicators of disease status and therapeutic response facilitates the application of effective treatment regimens on a more individualized basis.

A strong correlation between molecular abrogation during oncogenesis and changes in metabolic phenotype has been reported. For example, in various cancers AKT-induced activation of aerobic glycolysis is observed through induction of glycolytic enzymes (Elstrom et al., 2004, *Cancer Res*. 64:3892-3899; Young & Anderson, 2008, *Breast Cancer Res*. 10:202-209; DeBerardinis et al., 2008, *Curr. Opinion Genet. Develop*. 18:1-8). Furthermore, activation of the Ras/Raf/ERK/MAPK pathway leads to increased biosynthesis of phosphatidylcholine (the major membrane phospholipid) through up-regulation of choline kinase (Ronen et al., 2001, *Br. J. Cancer* 84:691-696; Beloueche-Babari et al., 2005, *Cancer Res*. 65:3356-3363). Additional specific metabolic markers for specific cancers have then been reported, for example without limitation, decreased N-acetyl aspartate in gliomas, decreased citrate in prostate cancer, and increased choline in breast cancer (Howe et al., 2003, *Magn. Reson. Med*. 49:223-232; Griffin & Shockcor, 2004, *Nat. Rev*. 4:551-561; Glude & Serkova, 2006, *Pharmacogenomics* 7:1109-1123; Serkova et al., 2007, *Curr. Opin. Mol. Ther*. 9:572-585). Because metabolic changes often precede detectable changes in tumor burden, metabolic changes are particularly useful as early indicators of disease and therapeutic efficacy. However, few studies investigating the utility of metabolic biomarkers in patients with acute leukemia have been reported. Nuclear magnetic resonance (NMR) spectroscopy is a technique to observe and quantify global and targeted metabolic changes in biological specimens, such as tissue biopsies and body fluids. Once established ex vivo, metabolites levels can be translated into non-invasive in vivo magnetic resonance spectroscopy (MRS) protocols (Serkova et al., 2007, Id.).

Magnetic resonance imaging (MRI) is a widely used clinical radiological modality which is a highly regarded standard for detection and follow-up of malignant tumors. With exquisite contrast resolution and ability to differentiate hematopoietic and fatty marrow, MRI is an important technique for evaluating the bone marrow non-invasively. The appearance of bone marrow in MR images depends on the pulse sequence selection and the relative amounts of cellularity, protein, water, and fat within the bone marrow. For example, spin-echo and fat-suppressed sequences have been most widely used to image bone marrow (Vogler & Murphy, 1998, *Radiology* 168:679-693). On T1-weighted MRI, fatty (yellow) bone marrow has higher T1-signal intensity than red bone marrow (hematopoietic). Pediatric bone marrow can display different patterns of MR signal intensity relative to adult (Mazumdar et al., 2002, *Am. J. Roent*. 179:1261-1266; Steinbach, 2007, *Am. J. Roent*. 188:1443-1445). Furthermore, the use of contrast-enhanced MRI can improve lesion conspicuity. For example, normal marrow shows minimal enhancement after administration of gadolinium chelate agents. By comparison, many malignant neoplasms exhibit an increase in signal intensity that is greater than the increase shown by normal marrow and by benign lesions.

BRIEF SUMMARY OF THE INVENTION

Provided herein are, inter alia, methods for determining the presence of leukemia cells in a subject and determining the change in the number of leukemia cells or the number of progenitor leukemia cells in the subject with time. The number of leukemia cells or the number of progenitor leukemia cells may change as the result of the regular course of a disease, or as a result of therapeutic intervention in a disease. In a first aspect, there is provided a method of determining whether a change in the number of leukemia cells or the number of progenitor leukemia cells occurs or will occur over time in the bone marrow of a subject. The method includes obtaining a first magnetic resonance image of the bone marrow of the subject at a first time point. Subsequently a second magnetic resonance image of the bone marrow is obtained at a second time point. The first magnetic resonance image is compared to the second magnetic resonance image, thereby determining whether a change in the number of leukemia cells or the number of progenitor leukemia cells occurred between the first time point and the second time point or will occur after said second time point.

In another aspect, there is provided a method for determining whether a tissue in a subject contains a plurality of leukemia cells or a plurality progenitor leukemia cells. The method includes detecting a level of an endogenous marker biomolecule in the tissue. The endogenous marker biomolecules may be one or more of aromatic acids, nucleotides, polyols, glycine, taurine, phosphocholine, glycerophosphocholine, choline, creatine, phosphocreatine, glutathione, glutamine, succinate, lysine, arginine, alanine, lactate, hydroxybutyrate, uridine diphosphoglucose, glycerophosphoethanolamine, monounsaturated fatty acids, glycerol phospholipids, total cholines, $(CH_2)_n$-lipids, total lipids, myo-inositol, glutamate, acetate, valine, leucine, isoleucine, adenosine triphosphate, adenosine diphosphate, nicotinamide adenine dinucleotide ($NAD^+$), phosphoethanolamine, phosphomonoesters, phosphodiesters, phosphatidylinositol, phosphatidylcholine, polyunsaturated fatty acids, fatty acids, cholesterol, adenosine, citrate, or triacylglycerol. The level of the endogenous marker biomolecule is compared to a standard control. If a higher level of nucleotides, glycine, phosphocholine, choline, glutathione, succinate, alanine, lactate, hydroxybutyrate, uridine diphosphoglucose, monounsaturated fatty acids, fatty acids, glycerol phospholipids, total cholines, $(CH_2)_n$-lipids, total lipids, acetate, adenosine diphosphate, phosphoethanolamine, phosphomonoesters, phosphatidylinositol, phosphatidylcholine, polyunsaturated fatty acids, cholesterol, adenosine, or triacylglycerol is detected relative to the standard control, this indicates that the tissue contains a plurality of leukemia cells or plurality of progenitor leukemia cells. Alternatively, if a lower level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, adenosine triphosphate, nicotinamide adenine dinucleotide ($NAD^+$), phosphodiesters or citrate relative to the standard control is detected, this indicates that the tissue contains a plurality of leukemia cells or plurality of progenitor leukemia cells. In the case of blood tissue, a higher level of polyunsaturated fatty acids or cholesterol relative to the standard control indicates that the tissue contains a plurality of leukemia cells or a plurality of progenitor leukemia cells.

In another aspect, there is provided a method for determining whether a leukemia therapy administered to a subject decreased or is capable of decreasing the number of leukemia cells or the number of progenitor leukemia cells in a tissue of the subject. The method includes a step of detecting a level of an endogenous marker biomolecule in the tissue at a first time point. The endogenous marker biomolecule one or more of aromatic acids, nucleotides, polyols, glycine, taurine, phosphocholine, glycerophosphocholine, choline, creatine, phosphocreatine, glutathione, glutamine, succinate, lysine, arginine, alanine, lactate, hydroxybutyrate, uridine diphosphoglucose, glycerophosphoethanolamine, monounsaturated fatty acids, glycerol phospholipids, total cholines, $(CH_2)_n$-lipids, total lipids, myo-inositol, glutamate, acetate, valine, leucine, isoleucine, adenosine triphosphate, adenosine diphosphate, nicotinamide adenine dinucleotide ($NAD^+$), phosphoethanolamine, phosphomonoesters, phosphodiesters, phosphatidylinositol, phosphatidylcholine, polyunsaturated fatty acids, fatty acids, cholesterol, adenosine, citrate or triacylglycerol. In a subsequent step, a leukemia therapy is administered to the subject. A level of the endogenous marker biomolecule in the tissue is then determined at a second time point. Thereafter, the level of the endogenous marker biomolecule at the first time point is compared to the level of the endogenous marker biomolecule at the second time point. A lower level of nucleotides, glycine, phosphocholine, choline, glutathione, succinate, alanine, lactate, hydroxybutyrate, uridine diphosphoglucose, monounsaturated fatty acids, fatty acids, glycerol phospholipids, total cholines, $(CH_2)_n$-lipids, total lipids, acetate, adenosine diphosphate, phosphoethanolamine, phosphomonoesters, phosphatidylinositol, phosphatidylcholine, polyunsaturated fatty acids, cholesterol, adenosine, or triacylglycerol at the second time point relative to the first time point indicates that the leukemia therapy decreased or is capable of decreasing the number of leukemia cells or the number of progenitor leukemia in a tissue of the subject. Alternatively, a higher level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, adenosine triphosphate, nicotinamide adenine dinucleotide ($NAD^+$), phosphodiesters or citrate at the second time point relative to the first time point indicates that the leukemia therapy administered to the subject decreased or is capable of decreasing the number of leukemia cells or the number of progenitor leukemia cells in the tissue of the subject. If the tissue is blood tissue, a lower level of polyunsaturated fatty acids or cholesterol relative to the standard control indicates that the leukemia therapy administered to the subject decreased or is capable of decreasing the number of leukemia cells or the number of progenitor leukemia cells in the tissue of the subject.

BRIEF DESCRIPTION OF THE DRAWINGS

FIG. 1A depicts a representative T1-weighted MR image of the iliac crest (top panels) and femur (bottom panels) of a leukemic MLL-AF9 Tg mouse ("MLL-AF9 Tg", right panels, T1=982 ms) and a WT littermate ("Wild-type", left panels, T1=1303 ms). FIG. 1B depicts quantitation of T1-weighted MRI signal intensities in bone marrow and muscle derived from the images of FIG. 1A. FIGS. 1A-1B Legend: BM: bone marrow; Msc: muscle; WT: wild-type; Tg: transgenic. Mean values disclosed in FIG. 1B were derived from a total of 8 slices taken from the left and right sides of the animal. FIG. 1C depicts ratios of bone marrow to muscle T1-weighted signal intensities for MLL-AF9 Tg mice and WT littermates. Mean values for individual mice were derived from 8 slices as described for FIG. 1B. Mean values derived from 6 individual mice are shown in FIG. 1C. FIG. 1C Legend: * Student's unpaired t test p value <0.0001; WT: solid; Tg: diagonal stripes.

FIG. 2A depicts a representative T1-weighted MR images of the femur pre- (top panels) and post- (bottom panels) administration of gadodiamide contrast agent in a leukemic MLL-AF9 Tg mouse and a WT littermate. FIG. 2B depicts fold-change in bone marrow and muscle MRI signal intensity demonstrating enhanced MRI signal intensity in bone marrow and muscle following administration of gadodiamide. Mean values (+/−SEM) are derived from 5 mice. The term "SEM" refers to the standard error of the mean, determined by dividing the standard deviation by the total number of cases in the frequency distribution. The change in signal intensity after administration of gadodiamide relative to baseline was not significantly different in bone marrow vs. muscle in WT or Tg mice, having student's unpaired t-test p=0.3062 or p=0.9780, respectively. FIG. 2C depicts ratio of bone marrow to muscle signal intensity for WT and Tg mice, before and after administration of contrast agent.

FIG. 3A depicts representative 40× images of bone marrow sections stained with H&E from a leukemic MLL-AF9 Tg mouse and a WT littermate. FIG. 3B depicts quantitation of bone marrow microvessel density in leukemic MLL-AF9 Tg mice and WT littermates. Mean values were derived from 5-6 mice. There was no significant difference in bone marrow microvessel density in WT and Tg mice; Student's unpaired t test p value=0.2805.

FIG. 4A depicts quantitation of bone marrow cell density in leukemic MLL-AF9 Tg mice and WT littermates. Mean values and standard errors were derived from 4 mice. Cell density was not significantly different in leukemic mice and healthy littermates; Student's unpaired t test p value=0.8211. FIG. 4B depicts quantitation of the fraction of proliferating bone marrow cells in leukemic MLL-AF9 Tg and WT littermates by visual inspection in a 40× field. Mean values were derived from 5 mice.

In FIGS. 5A-5C, the age of MLL-AF9 Tg mice at onset of overt leukemia varied between individuals, but was at least 16 weeks of age in all animals. FIG. 5A depicts ratios of bone marrow to muscle T1-weighted MRI signal intensities shown for MLL-AF9 Tg mice and WT littermates with time. Mean values were derived from 5-6 mice. Legend: * Student's paired t test p value <0.05 for WT verses Tg at indicated age; Φ Student's unpaired t test p value <0.005 for Tg mice at 10 verses 25 weeks of age. FIG. 5B depicts spleen volume in test mice with time, prior to and after onset of leukemia. FIG. 5C depicts peripheral white blood cell count in test mice with time, prior to and after onset of leukemia.

FIG. 6A: Wild-type mice. FIG. 6B: MLL-AF9 Tg transgenic mice. MR peak assignment: 1, $CH_3$-cholesterol; 2, $CH_3$-total lipids; 3, $(CH_2)_n$ of saturated fatty acids; 4, fatty acids (various $CH_2$); 5, polyunsaturated fatty acids; 6, phosphatidylethanolamine; 7, total cholines; 8, methanol; 9, phosphatidylcholine; 10, glycerol moieties from phospholipids and triacylglycerol; 11, residual water; 12, unsaturated fatty acids (including MUFA). The symbol "✕" denotes peaks derived from the solvent.

DETAILED DESCRIPTION OF THE INVENTION

I. Definitions

Figure 1A:
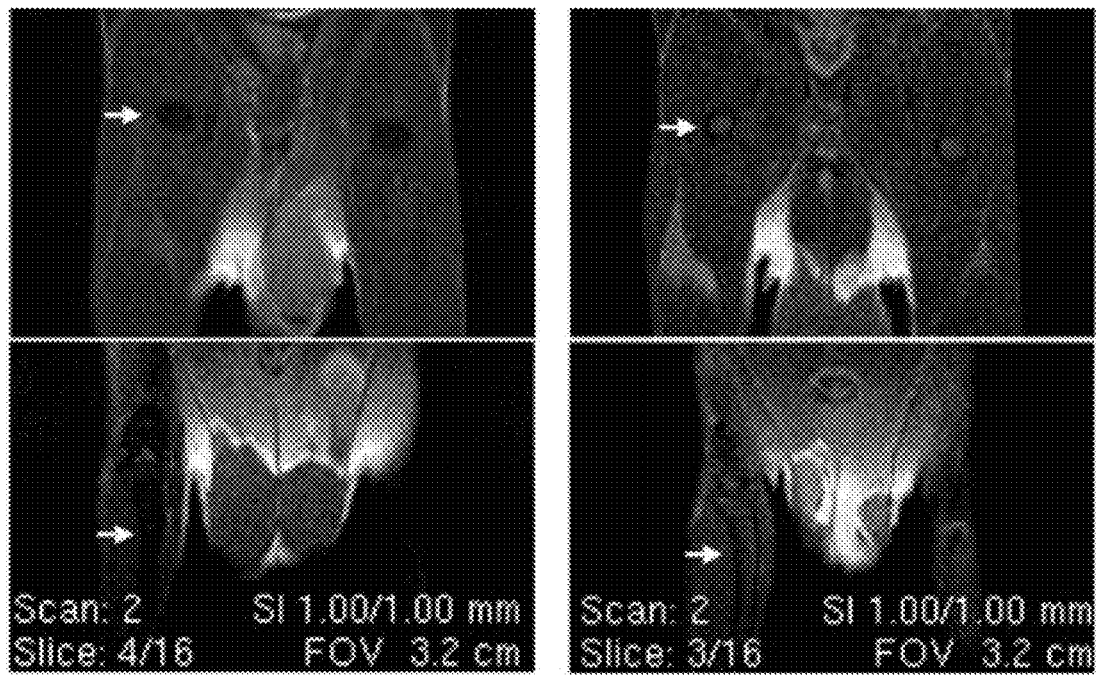
FIGS. 1A-1C depict differences in T1-weighted MRI signal intensity in bone marrow for MLL-AF9 transgenic (Tg) mice relative to wild-type (WT) mice.

The term "MR" refers to magnetic resonance and is the physical principle upon which a variety of experimental procedures known in the art and/or described herein are based, including MRI ("magnetic resonance imaging"), MRS ("magnetic resonance spectroscopy") and the like. The term "NMR" refers to "nuclear magnetic resonance." The terms "metabolic NMR" and the like refer to the use of NMR techniques in the study of metabolism, including quantitation of metabolite concentrations or relative levels in an animal or tissue.

The terms "T1" and "T2" used herein refer to the conventional meanings well known in the art (i.e., "spin-lattice relaxation time," and "spin-spin relaxation time," respectively).

The term "T1-weighted" in the context of MRI images refers to an image made with pulse spin echo or inversion recovery sequence, having appropriately shortened TR and TE, which as known in the art can demonstrate contrast between tissues having different T1 values. The term "TR" in this context refers to the repetition time between excitation pulses. The term "excitation pulse" is understood to refer to a 90-deg radio frequency (RF) excitation pulse. The term "TE" refers to the echo time between the excitation pulse and MR signal sampling.

The term "MLL-AF9" refers to the oncogene resulting from fusion of the MLL (mixed lineage leukemia) and AF9 genes, as described for example by Dobson and co-workers (Dobson et al., 1999, *EMBO J.* 18:3564-3574).

The term "Ki67" refers to the Ki67 antigen, which is a prototypic cell cycle related protein. The Ki67 antigen is expressed by proliferating cells in all phases of the active cell cycle including G1, S, G2 and M phase, but is absent in resting (G0) cells. Antibodies to the Ki67 antigen, made by methods well known in the art, are useful in establishing the cell growing fraction in neoplasms wherein, for example, immunohistochemical quantification is employed to determine the number of Ki67 positive cells among the total number of resting cells, giving the so-called "Ki67 index." It is believed that the correlation between low Ki67 index and histologically low-grade tumor is strong. Thus, Ki67 and antibodies thereto are routinely used as markers of cell cycling and cellular proliferation.

The term "subject" may be a mammalian subjects such as murine, rattus, equine, bovine, ovine, canine, feline or human. In some embodiments of the methods described herein, the subject is a mouse, while in other embodiments the subject is a human. The term "patient" in this context refers to a human subject.

The terms "treat," "treatment" and the like in the context of disease refer to ameliorating, suppressing, eradicating, and/or delaying the onset of the disease being treated. In some embodiments, the methods described herein are conducted with subjects in need of treatment. The terms "in need of treatment" and the like as used herein refer to a subject at risk for developing a disease, having a condition which would be understood by those of skill in the medical or veterinary arts as likely leading to a disease, and/or actually having a disease.

The term "anti-MAC1 antibody" refers to a monoclonal or polyclonal antibody directed against the MAC-1 antigen. As known in the art, the distribution of the MAC-1 antigen includes macrophages, bone marrow, spleen and natural killer cells. The terms "fluorescent labeled" and the like refer to attachment of a fluorescent label to a diagnostic reagent or naturally occurring macromolecule to facilitate identification and/or location of the reagent or macromolecule by methods well known in the art, including without limitation microscopy and flow cytometry.

II. Methods

In one aspect, there is provided an in vivo method of determining whether a change in the number of leukemia cells or the number of progenitor leukemia cells occurs or will occur over time in the bone marrow of a subject. The method includes obtaining a first magnetic resonance image of the bone marrow of the subject at a first time point. Subsequently, a second magnetic resonance image of the bone marrow is obtained at a second time point. The first magnetic resonance image is compared to the second magnetic resonance image, thereby determining whether a change in the number of leukemia cells or the number of progenitor leukemia cells occurred between the first time point and the second time point, or will occur after the second time point.

In one embodiment, there is provided an in vivo method of determining whether a change in the number of leukemia cells occurs over time in the bone marrow of a subject. The method includes obtaining a first magnetic resonance image of the bone marrow of the subject at a first time point. Subsequently, a second magnetic resonance image of the bone marrow is obtained at a second time point. The first magnetic resonance image is compared to the second magnetic resonance image, thereby determining whether a change in the number of leukemia cells occurred between the first time point and the second time point.

In certain embodiments, magnetic resonance images are obtained periodically, for example without limitation, every 1, 2, 3, 4, 5, 6 or 7 days, every 1, 2, 3 or 4 weeks, or every 1, 2, 3, 4, 5, 6, 7, 8, 9, 10, 11 or even 12 months. In certain embodiments, the first magnetic resonance image is obtained prior to the appearance of disease. A second magnetic resonance image may be obtained either prior to or subsequent to the appearance of disease. For example, magnetic resonance images were obtained every 3 weeks starting at 10 weeks of age for the subjects described in FIG. 5A. In certain embodiments, first, second and even subsequent magnetic resonance images are obtained ad hoc.

In one embodiment, a first signal intensity from the first magnetic resonance image and a second signal intensity from the second magnetic resonance image are determined. In this embodiment, comparing the first magnetic resonance image to the second magnetic resonance image includes comparing the first signal intensity to the second signal intensity. In some embodiments, the determination of signal intensity is made by methods routine in the art.

In certain embodiments, the method further includes administering a leukemia treatment to the subject in accordance with the change in the number of leukemia cells or the number of progenitor leukemia cells that will occur or has occurred.

In certain embodiments, the first magnetic resonance image is a first T1-weighted magnetic resonance image and the second magnetic resonance image is a second T1-weighted magnetic resonance image. In some further embodiments, a first T1-weighted signal intensity from the first T1-weighted magnetic resonance image and a second T1-weighted signal intensity from the second T1-weighted magnetic resonance image are determined. Then, the first T1-weighted signal intensity is compared to the second T1-weighted signal intensity.

In certain embodiments, a first T1-weighted relaxation time may be determined from the first T1-weighted magnetic resonance image and a second T1-weighted relaxation time may be determined from the second T1-weighted magnetic resonance image. Then, the first T1-weighted relaxation time and the second T1-weighted relaxation time may be compared.

In certain embodiments, the subject is a human subject. In other embodiments, the subject is not a human, such as a mouse. In certain embodiments (e.g. wherein the subject is a human subject), the first magnetic resonance image is a first T1-weighted magnetic resonance image and the second magnetic resonance image is a second T1-weighted magnetic resonance image. A first T1-weighted signal intensity may be determined from the first T1-weighted magnetic resonance image, and a second T1-weighted signal intensity may be determined from the second T1-weighted magnetic resonance image. The step of comparing the first magnetic resonance image to the second magnetic resonance image includes comparing the first T1-weighted signal intensity to the second T1-weighted signal intensity.

In certain embodiments, in the absence of administration of a leukemia treatment to the human subject, comparison of a higher second T1-weighted signal intensity relative to the first T1-weighted signal intensity indicates an increase in the number of leukemia cells or the number of progenitor leukemia cells that has occurred or will occur. In certain embodiments, in the absence of administration of a leukemia treatment to the human subject, comparison of a higher second T1-weighted signal intensity relative to the first T1-weighted signal intensity indicates an increase in the number of leukemia cells that has occurred or will occur. In certain embodiments, in the absence of administration of a leukemia treatment to the human subject, comparison of a higher second T1-weighted signal intensity relative to the first T1-weighted signal intensity indicates an increase in the number of progenitor leukemia cells that has occurred or will occur.

In certain embodiments, in the absence of administration of a leukemia treatment to the human subject, comparison of a higher second T1-weighted signal intensity relative to the first T1-weighted signal intensity indicates an increase in the number of leukemia cells or the number of progenitor leukemia cells. In certain embodiments, in the absence of administration of a leukemia treatment to the human subject, comparison of a higher second T1-weighted signal intensity relative to the first T1-weighted signal intensity indicates an increase in the number of leukemia cells. In certain embodiments, in the absence of administration of a leukemia treatment to the human subject, comparison of a higher second T1-weighted signal intensity relative to the first T1-weighted signal intensity indicates an increase in the number of progenitor leukemia cells.

In other embodiments, after obtaining a first magnetic resonance image of the bone marrow at a first time point and prior to obtaining a second magnet resonance image of the bone marrow at a second time, a leukemia treatment is administered to the human subject. A lower second T1-weighted signal intensity relative to the first T1-weighted signal intensity indicates a decrease in the number of leukemia cells or the number of progenitor leukemia cells has occurred or will occur. In some embodiments, a lower second T1-weighted signal intensity relative to the first T1-weighted signal intensity indicates a decrease in the number of leukemia cells has occurred or will occur. In some embodiments, a lower second T1-weighted signal intensity relative to the first T1-weighted signal intensity indicates a decrease in the number of progenitor leukemia cells has occurred or will occur. In a further embodiment, after obtaining a second magnetic resonance image at a second time point, administration of the leukemia treatment is ceased and a third magnetic resonance image of the bone marrow is obtained at a third time point. The third magnetic resonance image may be a third T1-weighted magnetic resonance image. The third T1-weighted signal intensity is compared to the second T1-weighted signal intensity. A higher third T1-weighted signal intensity relative to the second T1-weighted signal intensity indicates an increase in the amount of adipose tissue in the bone marrow that has occurred or will occur.

In other embodiments, after obtaining a first magnetic resonance image of the bone marrow at a first time point and prior to obtaining a second magnet resonance image of the bone marrow at a second time, a leukemia treatment is administered to the human subject. A lower second T1-weighted signal intensity relative to the first T1-weighted signal intensity indicates a decrease in the number of leukemia cells or the number of progenitor leukemia cells. In some embodiments, a lower second T1-weighted signal intensity relative to the first T1-weighted signal intensity indicates a decrease in the number of leukemia cells. In some embodiments, a lower second T1-weighted signal intensity relative to the first T1-weighted signal intensity indicates a decrease in the number of progenitor leukemia cells. In a further embodiment, after obtaining a second magnetic resonance image at a second time point, administration of the leukemia treatment is ceased and a third magnetic resonance image of the bone marrow is obtained at a third time point. The third magnetic resonance image may be a third T1-weighted magnetic resonance image. The third T1-weighted signal intensity is compared to the second T1-weighted signal intensity. A higher third T1-weighted signal intensity relative to the second T1-weighted signal intensity indicates an increase in the amount of adipose tissue in the bone marrow.

In another embodiment, a first T1-weighted relaxation time is determined from the first T1-weighted magnetic resonance image, and a second T1-weighted relaxation time is determined from the second T1-weighted magnetic resonance image. The T1-weighted relaxation time of the first magnetic resonance image is compared to the T1-weighted relaxation time of the second magnetic resonance image. In the absence of administration of a leukemia treatment to the human subject, a lower second T1-weighted relaxation time relative to the first T1-weighted relaxation time indicates an increase in the number of leukemia cells or the number of progenitor leukemia cells has occurred or will occur. In some embodiments, a lower second T1-weighted relaxation time relative to the first T1-weighted relaxation time indicates an increase in the number of leukemia cells has occurred or will occur. In some embodiments, a lower second T1-weighted relaxation time relative to the first T1-weighted relaxation time indicates an increase in the number of progenitor leukemia cells has occurred or will occur.

In another embodiment, a first T1-weighted relaxation time is determined from the first T1-weighted magnetic resonance image, and a second T1-weighted relaxation time is determined from the second T1-weighted magnetic resonance image. The T1-weighted relaxation time of the first magnetic resonance image is compared to the T1-weighted relaxation time of the second magnetic resonance image. In the absence of administration of a leukemia treatment to the human subject, a lower second T1-weighted relaxation time relative to the first T1-weighted relaxation time indicates an increase in the number of leukemia cells or the number of progenitor leukemia cells. In some embodiments, a lower second T1-weighted relaxation time relative to the first T1-weighted relaxation time indicates an increase in the number of leukemia cells. In some embodiments, a lower second T1-weighted relaxation time relative to the first T1-weighted relaxation time indicates an increase in the number of progenitor leukemia cells.

In certain embodiments, after obtaining a first magnetic resonance image of the bone marrow at a first time point and prior to obtaining a second magnet resonance image of the bone marrow at a second time, a leukemia treatment is administered to the human subject. A higher second T1-weighted relaxation time relative to the first T1-weighted relaxation time indicates a decrease in the number of leukemia cells or the number of progenitor leukemia cells that has occurred or will occur. In some embodiments, a higher second T1-weighted relaxation time relative to the first T1-weighted relaxation time indicates a decrease in the number of leukemia cells that has occurred or will occur. In some embodiments, a higher second T1-weighted relaxation time relative to the first T1-weighted relaxation time indicates a decrease in the number of progenitor leukemia cells that has occurred or will occur. In a further embodiment, after obtaining a second magnetic resonance image of the bone marrow at a second time point, administration of the leukemia treatment is ceased, and a third magnetic resonance image of the bone marrow is obtained at a third time point. The third magnetic resonance image is a third T1-weighted magnetic resonance image, from which a third T1-weighted relaxation time is calculated. The relaxation time of the third T1-weighted magnetic resonance image is compared to the second T1-weighted relaxation time. A lower third T1-weighted relaxation time relative to the second T1-weighted relaxation time indicates an increase in the amount of adipose tissue in the bone marrow that has occurred or will occur.

In another embodiment, the method further includes administering a leukemia treatment to the subject in accordance with the change in the number of adipose cells that has occurred or will occur.

In certain embodiments, after obtaining a first magnetic resonance image of the bone marrow at a first time point and prior to obtaining a second magnet resonance image of the bone marrow at a second time, a leukemia treatment is administered to the human subject. A higher second T1-weighted relaxation time relative to the first T1-weighted relaxation time indicates a decrease in the number of leukemia cells or the number of progenitor leukemia cells. In some embodiments, a higher second T1-weighted relaxation time relative to the first T1-weighted relaxation time indicates a decrease in the number of leukemia cells. In some embodiments, a higher second T1-weighted relaxation time relative to the first T1-weighted relaxation time indicates a decrease in the number of progenitor leukemia cells. In a further embodiment, after obtaining a second magnetic resonance image of the bone marrow at a second time point, administration of the leukemia treatment is ceased, and a third magnetic resonance image of the bone marrow is obtained at a third time point. The third magnetic resonance image is a third T1-weighted magnetic resonance image, from which a third T1-weighted relaxation time is calculated. The relaxation time of the third T1-weighted magnetic resonance image is compared to the second T1-weighted relaxation time. A lower third T1-weighted relaxation time relative to the second T1-weighted relaxation time indicates an increase in the amount of adipose tissue in the bone marrow.

In another aspect, there is provided a method for determining whether a tissue in a subject contains a plurality of leukemia cells or a plurality progenitor leukemia cells. The method includes detecting a level of an endogenous marker biomolecule in the tissue. The endogenous marker biomolecule is chosen from the following list: aromatic acids, nucleotides, polyols, glycine, taurine, phosphocholine, glycerophosphocholine, choline, creatine, phosphocreatine, glutathione, glutamine, succinate, lysine, arginine, alanine, lactate, hydroxybutyrate, uridine diphosphoglucose, glycerophosphoethanolamine, monounsaturated fatty acids, glycerol phospholipids, total cholines, $(CH_2)_n$-lipids, total lipids, myo-inositol, glutamate, acetate, valine, leucine, isoleucine, adenosine triphosphate, adenosine diphosphate, nicotinamide adenine dinucleotide ($NAD^+$), phosphoethanolamine, phosphomonoesters, phosphodiesters, phosphatidylinositol, phosphatidylcholine, polyunsaturated fatty acids, fatty acids, cholesterol, adenosine, citrate, or triacylglycerol. The level of the endogenous marker biomolecule is compared to a standard control. If a higher level of nucleotides, glycine, phosphocholine, choline, glutathione, succinate, alanine, lactate, hydroxybutyrate, uridine diphosphoglucose, monounsaturated fatty acids, fatty acids, glycerol phospholipids, total cholines, $(CH_2)_n$-lipids, total lipids, acetate, adenosine diphosphate, phosphoethanolamine, phosphomonoesters, phosphatidylinositol, phosphatidylcholine, polyunsaturated fatty acids, cholesterol, adenosine, or triacylglycerol is detected relative to the standard control, then this indicates that the tissue contains a plurality of leukemia cells or plurality of progenitor leukemia cells. Alternatively, if a lower level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, adenosine triphosphate, nicotinamide adenine dinucleotide ($NAD^+$), phosphodiesters or citrate relative to the standard control is detected, this indicates that the tissue contains a plurality of leukemia cells or plurality of progenitor leukemia cells. In some embodiments, if a lower level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, phosphodiesters or citrate relative to the standard control is detected, this indicates that the tissue contains a plurality of leukemia cells or plurality of progenitor leukemia cells. In the case of blood tissue, a higher level of polyunsaturated fatty acids or cholesterol relative to the standard control indicates that the tissue contains a plurality of leukemia cells or a plurality of progenitor leukemia cells. In certain embodiments, the method is conducted in vivo. In other embodiments, the method is conducted ex vivo on tissue, for example, explanted from the subject.

The terms "progenitor," "progenitor cell" and the like in the context of disease (for example, leukemia) refer to cells which can eventually acquire the diseased state. In some embodiments, the term "plurality" in the context of leukemia cells and/or progenitor leukemia cells refers to a detectable plurality which is detectable by the methods described herein and/or by methods known in the art.

The level of the endogenous marker biomolecule in the tissue may be detected at a first time point. Prior to the first time point, the level of the endogenous marker biomolecule in the tissue may be detected at a control time point. In this case, the level of the endogenous marker biomolecule in the tissue at the control time point is the standard control.

In some embodiments, the standard control is the level of a metabolite present at approximately the same levels in each of a population of the subjects. In other embodiments, the standard control is approximately the average level of the endogenous marker biomolecule present in a population of the subjects. In certain embodiments, the term "population of the subjects" refers to subjects lacking disease, for example subjects not having leukemia.

In another aspect, there is provided a method of determining whether a leukemia therapy administered to a subject decreased or is capable of decreasing the number of leukemia cells or the number of progenitor leukemia cells in a tissue of the subject. The method includes a step of detecting a level of an endogenous marker biomolecule in the tissue at a first time point. The endogenous marker biomolecule is chosen from the following list: aromatic acids, nucleotides, polyols, glycine, taurine, phosphocholine, glycerophosphocholine, choline, creatine, phosphocreatine, glutathione, glutamine, succinate, lysine, arginine, alanine, lactate, hydroxybutyrate, uridine diphosphoglucose, glycerophoethanolamine, monounsaturated fatty acids, fatty acids, glycerol phospholipids, total cholines, $(CH_2)_n$-lipids, total lipids, myo-inositol, glutamate, acetate, valine, leucine, isoleucine, adenosine triphosphate, adenosine diphosphate, nicotinamide adenine dinucleotide ($NAD^+$), phosphoethanolamine, phosphomonoesters, phosphodiesters, phosphatidylinositol, phosphatidylcholine, polyunsaturated fatty acids, cholesterol, adenosine, citrate or triacylglycerol. In a subsequent step, a leukemia therapy is administered to the subject. In yet another subsequent step, a level of the endogenous marker biomolecule in the tissue is determined at a second time point. Then, the levels of the endogenous marker biomolecule at the first time point is compared to the level of the endogenous marker biomolecule at the second time point. After this comparison, a lower level of nucleotides, glycine, phosphocholine, choline, glutathione, succinate, alanine, lactate, hydroxybutyrate, uridine diphosphoglucose, monounsaturated fatty acids, fatty acids, glycerol phospholipids, total cholines, $(CH_2)_n$-lipids, total lipids, acetate, adenosine diphosphate, phosphoethanolamine, phosphomonoesters, phosphatidylinositol, phosphatidylcholine, polyunsaturated fatty acids, cholesterol, adenosine, or triacylglycerol at the second time point relative to the first time point, indicates that the leukemia therapy decreased or is capable of decreasing the number of leukemia cells or the number of progenitor leukemia cells in the tissue of the subject. Alternatively, a higher level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, adenosine triphosphate, nicotinamide adenine dinucleotide ($NAD^+$), phosphodiesters or citrate at the second time point relative to the first time point, indicates that the leukemia therapy administered to the subject decreased or is capable of decreasing the number of leukemia cells or the number of progenitor leukemia cells in the tissue of the subject. In some embodiments, a higher level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, phosphodiesters or citrate at the second time point relative to the first time point, indicates that the leukemia therapy administered to the subject decreased or is capable of decreasing the number of leukemia cells or the number of progenitor leukemia cells in the tissue of the subject. If the tissue is blood tissue, a lower level of polyunsaturated fatty acids or cholesterol relative to the standard control indicates that the leukemia therapy administered to the subject decreased or is capable of decreasing the number of leukemia cells or the number of progenitor leukemia cells in the blood tissue of the subject. In some embodiments, a lower level of polyunsaturated fatty acids or cholesterol relative to the standard control indicates that the leukemia therapy administered to the subject decreased or is capable of decreasing the number of leukemia cells in the blood tissue of the subject. In some embodiments, a lower level of polyunsaturated fatty acids or cholesterol relative to the standard control indicates that the leukemia therapy administered to the subject decreased or is capable of decreasing the number of progenitor leukemia cells in the blood tissue of the subject. In certain embodiments, the method further includes continuing administration of the leukemia therapy to the subject.

In certain embodiments, there is provided a method of determining whether a leukemia therapy administered to a subject decreased the number of leukemia cells or the number of progenitor leukemia cells in a tissue of the subject. The method includes a step of detecting a level of an endogenous marker biomolecule in the tissue at a first time point. The endogenous marker biomolecule is chosen from the following list: aromatic acids, nucleotides, polyols, glycine, taurine, phosphocholine, glycerophosphocholine, choline, creatine, phosphocreatine, glutathione, glutamine, succinate, lysine, arginine, alanine, lactate, hydroxybutyrate, uridine diphosphoglucose, glycerophosphoethanolamine, monounsaturated fatty acids, glycerol phospholipids, total cholines, $(CH_2)_n$-lipids, total lipids, myo-inositol, glutamate, acetate, valine, leucine, isoleucine, adenosine triphosphate, adenosine diphosphate, nicotinamide adenine dinucleotide ($NAD^+$), phosphoethanolamine, phosphomonoesters, phosphodiesters, phosphatidylinositol, phosphatidylcholine, polyunsaturated fatty acids, fatty acids, cholesterol, adenosine, citrate or triacylglycerol. In a subsequent step, a leukemia therapy is administered to the subject. In yet another subsequent step, a level of the endogenous marker biomolecule in the tissue is determined at a second time point. Then, the levels of the endogenous marker biomolecule at the first time point is compared to the level of the endogenous marker biomolecule at the second time point. After this comparison, a lower level of nucleotides, glycine, phosphocholine, choline, glutathione, succinate, alanine, lactate, hydroxybutyrate, uridine diphosphoglucose, monounsaturated fatty acids, fatty acids, glycerol phospholipids, total cholines, $(CH_2)_n$-lipids, total lipids, acetate, adenosine diphosphate, phosphoethanolamine, phosphomonoesters, phosphatidylinositol, phosphatidylcholine, polyunsaturated fatty acids, cholesterol, adenosine or triacylglycerol at the second time point relative to the first time point, indicates that the leukemia therapy decreased the number of leukemia cells or the number of progenitor leukemia cells. Alternatively, a higher level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, adenosine triphosphate, nicotinamide adenine dinucleotide ($NAD^+$), phosphodiesters or citrate at the second time point relative to the first time point, indicates the leukemia therapy administered to the subject decreasing the number of leukemia cells or the number of progenitor leukemia cells in the tissue of the subject. In some embodiments, a higher level of aromatic acids, polyols, taurine, glycerophosphocholine, creatine, phosphocreatine, glutamine, lysine, arginine, glycerophosphoethanolamine, myo-inositol, glutamate, valine, leucine, isoleucine, phosphodiesters or citrate at the second time point relative to the first time point, indicates that the leukemia therapy administered to the subject decreased the number of leukemia cells or the number of progenitor leukemia cells in the tissue of the subject. If the tissue is blood tissue, a lower level of polyunsaturated fatty acids or cholesterol relative to the standard control indicates that the leukemia therapy administered to the subject decreased the number of leukemia cells or the number of progenitor leukemia cells in the blood tissue of the subject. In some embodiments, a lower level of polyunsaturated fatty acids or cholesterol relative to the standard control indicates that the leukemia therapy administered to the subject decreased the number of leukemia cells in the blood tissue of the subject. In some embodiments, a lower level of polyunsaturated fatty acids or cholesterol relative to the standard control indicates that the leukemia therapy administered to the subject decreased the number of progenitor leukemia cells in the blood tissue of the subject. In certain embodiments, the method further includes continuing administration of the leukemia therapy to the subject.

In certain embodiments, the tissue is blood tissue, spleen tissue, or bone marrow. tissue. Where the tissue is blood tissue, the endogenous marker biomolecule may be adenosine, citrate, succinate, lactate, monounsaturated fatty acids, triacylglycerol, phosphatidylinositol, phosphatidylcholine, total cholines, polyunsaturated fatty acids, $(CH_2)_n$-lipids, total lipids, fatty acids or cholesterol. In some embodiments, a plurality of endogenous marker biomolecules are detected and compared.

In certain embodiments, if the tissue is spleen tissue, then the endogenous marker biomolecule is aromatic acids, nucleotides, polyols, glycine, taurine, phosphocholine, glycerophosphocholine, choline, creatine, phosphocreatine, glutathione, glutamine, succinate, lysine, arginine, alanine, lactate, hydroxybutyrate, uridine diphosphoglucose, glycerophosphoethanolamine, monounsaturated fatty acids, glycerol phospholipids, total cholines, $(CH_2)_n$-lipids, or total lipids. In some embodiments, a plurality of these endogenous marker biomolecules are detected and compared.

In some embodiments, if the tissue is bone marrow tissue then the endogenous marker biomoecule is myo-inositol, glutamine, glutamate, acetate, alanine, lactate, valine, leucine, isoleucine, adenosine triphosphate, adenosine diphosphate, nicotinamide adenine dinucleotide (NAD+), uridine diphosphoglucose, phosphocholine, phosphoethanolamine, glycerophosphocholine, glycerophosphoethanolamine, phosphomonoesters, phosphodiesters, monounsaturated fatty acids, glycerol phospholipids, phosphatidylinositol, phosphatidyl choline and/or $(CH_2)_n$-lipids, or a combination thereof.

In some embodiments, the levels of alanine, phosphomonoester and/or phosphodiester are detected. In other embodiments, the levels of phosphatidylcholine, glycerol phospholipids and/or phosphomonoester are detected. In some embodiments, the level of hydroxybutyrate is detected. In other embodiments, the levels of valine, leucine, and/or isoleucine are detected.

Detecting the level of the endogenous marker biomolecule may include detecting the levels of a plurality of endogenous marker biomolecules as described herein, for example without limitation, 2, 3, 4, 5, 6, 7, 8, 9 or even 10 endogenous marker biomolecules. The terms "detecting" and the like in the context of the methods described herein refer to the qualitative and/or quantitative detection of a molecule by any appropriate method. Examples of useful detection methods include mass spectrometry, gas chromatograph, direct chemical analysis, US/VIS spectrophotometry, and/or any appropriate NMR method (e.g. one-dimensional NMR (1D-NMR), two-dimensional NMR (2D-NMR), MRI, MRS, and other NMR methods known to those skilled in the art).

In some embodiments, where the detection method involved an NMR method (such as MRI or MRS), a contrast agent may be used. The terms "enhancement agent," "contrast agent," "contrast media" and the like in the context of MR imagery refers to chemical compounds and/or compositions which alter the magnetic relaxation properties of a subject or tissue in order to more clearly define structures within the subject or tissue, as known in the art. Without wishing to be bound by theory, it is believed that such agents and media modulate spin-lattice and/or spin-spin relaxation. Exemplary agents include without limitation, gadolinium-based compounds (for example, Omniscan™, Multihance®, Magnevist®, ProHance®, Vasovist®, OptiMARK®), iron oxide compounds (for example, Cliavist™, Combidex®, Endorem®, Feridex, Resovist®, Sinerem®), manganese chelates, and the like as known in the art.

EXAMPLES

Materials and Methods
MLL-AF9 Tg Mice.
MLL-AF9 transgenic (Tg) mice used for experiments were backcrossed onto the C57B1/6 background for 3-5 generations, as well known in the art. All experiments involving animals conformed to the relevant regulatory standards as approved by the University of Colorado Institutional Animal Use and Care Committee.

Evaluation of Onset and Progression of Leukemia.

To assess onset and progression of leukemia, blood samples (50-100 μL) were collected from the orbital venous sinus into EDTA-coated tubes and total WBC counts were determined using a Hemavet® 950FS hematology system (Drew Scientific, Oxford, Conn.). Alternatively, red blood cells were lysed by treatment with Gey's solution (155 mM ammonium chloride, 10 mM potassium bicarbonate) for 5 minutes, peripheral blood mononuclear cells were stained with fluorescent-labeled anti-MAC1 antibody (#553310, BD Pharmingen, San Jose, Calif.), and stained cells were analyzed by flow cytometry to determine the percentage of peripheral blasts Magnetic Resonance Imaging Animals underwent MRI evaluations every 2-3 weeks starting at 10 weeks of age. Mice were anesthetized with 2% inhaled isoflurane or 80 mg/kg ketamine and 12 mg/kg xylazine injected intraperitoneally. Anesthetized animals were placed in a prone position on a plastic board with their hind limbs extended and held in place with nylon tubing. Coronal rapid acquisition with relaxation enhancement (RARE) T1-weighted MR images were obtained using a 4.7 Tesla Bruker PharmaScan® equipped with a 38 mm volume transmitter/receiver coil (Bruker Biospin, Billerica, Mass.). The following MR parameters were used for determination of bone marrow signal intensity and spleen size: field of view (FOV) 3.20 cm; repetition time/echo time (TR/TE) 720/11 msec, slice thickness 1 mm, flip angle 90°, number of averages 4, matrix size 256×256. Where indicated, a 27G catheter was placed in the tail vein prior to imaging for gadolinium injection. After baseline images were obtained, Omniscan™ (GE Healthcare, Piscataway, N.J.), a commercially available gadodiamide contrast agent, was injected into the tail-vein catheter over approximately 5 seconds without moving the animal and the MRI scan was repeated 3 minutes later to assess contrast uptake in the bone marrow. At the end of the study (between 20 and 25 weeks of age), T1-mapping using RARE sequence with various repetition times (e.g., 400, 600, 800, 1000, 1200, 1400 ms) was used for precise calculation of T1-relaxation times. No contrast agent was injected and no fat suppression was applied for T1-mapping. The term "T1-mapping" refers to MRI techniques wherein signal recovery after a preparation pulse is sampled with time during multiple measurements, and the associated relaxation time is calculated for every element of an image, resulting in the so-called "T1 map."

All images were processed using Bruker ParaVision software (version PV3.0.2). For the series of T1-weighted images with six repetition times, a low-volume ROI (region of interest) was placed onto the bone marrow of femurs on a corresponding slice for each set of TR series. The signal intensity of an MR image is proportional to tissue T1 and T2 relaxation times, as well as applied repetition and echo times. Thus, for the series of multiple repetition times in the MR protocol, the so-called Bruker "T1sat-fitting function" based on the equations following was applied in order to calculate T1 relaxation time as a function of signal intensity and TR values of each image:

$$S = M_0(1 - e^{-TR/T1})e^{-TE/T2} \quad (1)$$

or for T1-fitting only $$S = C1\, e^{-TR/T1} \quad (2)$$

wherein $C1 = M_0(1 - e^{-TE/T2})$ is a constant which gets fitted. All calculated T1 times are given in milliseconds (ms).

For determination of signal intensity, ROIs were placed onto bone marrow (e.g., femurs, iliac crests and the like) and muscle and signal intensities were determined. Mean signal intensities, mean relative signal intensities, and standard errors for individual mice were derived from 8-10 slices. 3D-ROIs were used to determine spleen volumes (in mm³).

Determination of Bone Marrow Microvessel Density, Cell Density and Proliferative Index Femurs and tibia were collected from leukemic MLL-AF9 Tg mice and WT littermates and fixed in 10% phosphate-buffered formalin at room temperature for 48 hours, as routine in the art. Fixed bones were stored in 70% ethanol prior to decalcification by methods known in the art. Decalcified samples were embedded in paraffin, sectioned, and mounted. Sections were stained with hematoxylin and eosin (H&E) as known in the art, or sections were strained using a Ki67 staining protocol as known in the art. Bone marrow microvessel density, cell density, and fraction of Ki67 positive-cells were quantitated by microscopic inspection, for example at 40× magnification.

Collection and Extraction of Bone Marrow for Metabolic MRS

Before collection of tissues for metabolic NMR, the animals were fasted overnight and then injected with 250 mg/kg of [1-$^{13}$C] glucose via tail vein (total injection volume not to exceed 150 μl). First, about 200 μl blood was collected into heparinized tubes through straight heart stick, placed on ice and rapidly stored at −80° C. prior to further processing. The spleen was resected and immediately frozen in liquid nitrogen, followed by −80° C. storage. Femurs and tibia were collected, and bone marrow was flushed out with cold phosphate buffer saline (PBS). Bone marrow cells were collected by centrifugation at 1200×G in a refrigerated microcentrifuge and frozen with liquid nitrogen. Samples were stored at −80° C. prior to further processing. Samples collected from individual mice were analyzed separately, or samples from 2-3 mice were pooled prior to extraction to precipitate proteins and separate water-soluble and lipid metabolites. Spleen and bone marrow samples were extracted with 12% perchloric acid (PCA) and processed as previously described (Serkova et al., 2006, *J Hepatol.* 44:956-962). Heparinized whole blood was extracted using dual methanol/chloroform extraction as described. See Serkova et al., 2005, *Kidney Int.* 67:1142-1151. Water-soluble extracts were dissolved in 0.5 ml of deuterium oxide (D$_2$O) and lipid extracts in 0.6 ml of deuterated methanol/chloroform mixture for subsequent MR analysis.

Quantitative Metabolic MRS Analysis

All high-resolution NMR studies were performed at the University of Colorado Cancer Center Metabolomics core facility. For $^1$H- and $^{13}$C-NMR, a Bruker 500 DRX spectrometer was used with a conventional Bruker TXI or 1-mm microprobe for low-volume samples. For chemical shift reference and quantification of metabolites, an external standard (d-trimethyl silyl propionic acid, TSP, at 0 ppm) was used. Metabolites were identified by 2-dimensional NMR and referred with a chemical shift data base (Rudolph et al., 2006, *Physiol. Genomics* 28:323-326; Serkova et al., 2005, Id.; Serkova & Niemann, 2006, *Exprt. Rev. Mol. Diagn.* 6:717-731). All $^{31}$P-MRS was acquired using a 300 MHz Bruker spectrometer with a 5-mm QNP probe after addition of 100 mM EDTA to complex divalent cations. Methylene diphosphoric acid (18 ppm) was used as a chemical shift reference for quantification of phosphor metabolites. Data analysis was performed using Bruker 1DWINNMR software for line broadening, exponential multiplication, Fourier transformation, phase and baseline correction, calibration and integration.

Statistical Analysis

Statistical analysis was performed using Graphpad Prism® v4.0 software (Graphpad Software, Inc., San Diego, Calif.). All quantitative data are given as mean+/−standard error based on the number of replicates in each group. Significant differences were determined using the unpaired Student's t-test and the F test was used to compare variances. P values <0.05 were considered statistically significant.

Experimental

The following examples are provided to illustrate but not limit the methods disclosed herein. The following abbreviations are used herein: PC: phosphocholine; GP: glycerophospho; GPC: glycerophosphocholine; Cho: choline; Cr: creatine; Eth: ethanolamine; PCr: phosphocreatine; GSH: glutathione; MUFA: monounsaturated fatty acid; TAG: triacyl glycerol; Plipids: phospholipids; Ptd: phosphatidyl; PUFA: polyunsaturated fatty acids; PtdIns: phosphatidylinositol; PtdCho: phosphatidylcholine; PEth: phosphoethanolamine; PCho: phosphocholine; PME: phosphate monoester; PDE: phosphate diester; MUFA: mono-unsaturated fatty acid.

Example 1

Detection of Bone Marrow Changes with Weighted MRI and T1 Mapping

MLL-AF9 Tg mice develop acute leukemias that have many features in common with the high-risk MLL-rearranged leukemias in humans, including relative frequencies of acute myeloid leukemias (AMLs) and acute lymphoid leukemias (ALLs), sites of organ infiltration, and AML morphologies consistent with FAB M4 and M5 subtypes as known in the art (Dobson et al., 1999, Id.; Johnson et al., 2003, *Blood* 101:3229-3235; Schoch et al., 2003, *Blood* 102: 2395-2402). Acute leukemia develops in MLL-AF9 Tg mice at a median age of 5 months, indicating that secondary genetic events are required for leukemogenesis. Thus, the tumors arising in individual MLL-AF9 Tg mice are presumably genetically distinct. These observations suggest that MLL-AF9 Tg mice represent a good model of acute leukemia in humans.

Figure 1B:
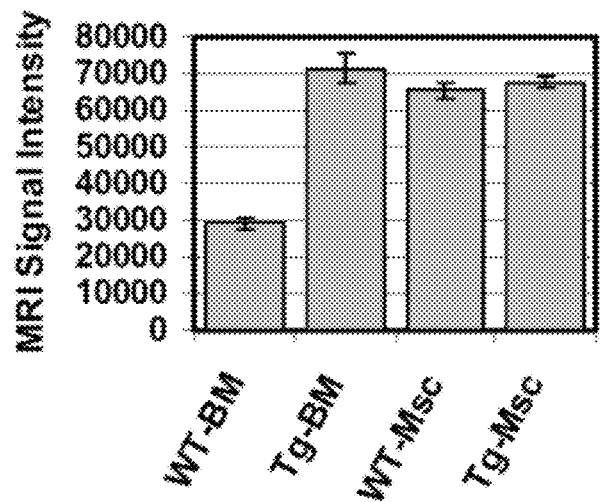

To investigate the utility of MRI for detection of bone marrow changes associated with development of leukemia, high-resolution T1-weighted MR images of bone marrow in MLL-AF9 Tg mice with overt leukemia and in WT littermates (lacking overt leukemia) were generated. The term "overt leukemia" as used herein refers to >75% peripheral blasts as determined by histological methods known in the art and/or described herein. Leukemic MLL-AF9 Tg mice exhibited a statistically significant increase (~65%) in T1-weighted MRI signal intensity in bone marrow compared with WT controls as exemplified in FIG. 1A. In contrast, as depicted in FIG. 1B, muscle MRI signal intensity was similar in Tg mice and WT under the experimental conditions.

Figure 1C:
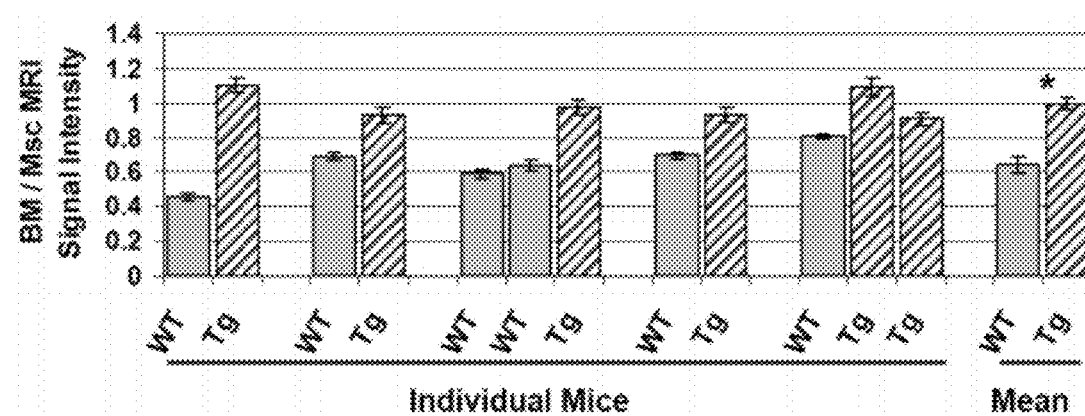
Figure 1D:
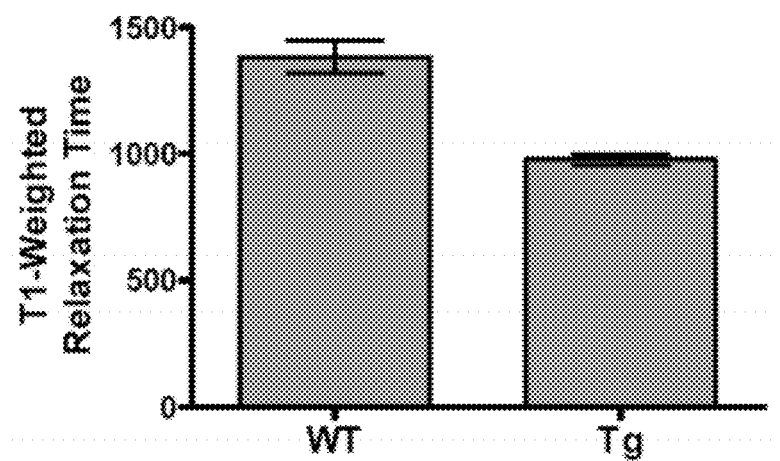
FIG. 1D depicts bone marrow T1-relaxation times determined by Bruker T1-mapping using the RARE sequence with repetition times of 400, 600, 800, 1000, 1200 and 1400 msec. Mean values and standard errors were derived from 4 mice. Student's unpaired t test p value=0.0010.

Bone marrow T1-relaxation times were also determined by T1-mapping using six different repetition times. Mean T1-relaxation times in wild-type mice were 1303±168 ms compared with 982±40 ms in MLL-AF9 Tg littermates (n=4; p=0.0010). In contrast, no significant differences in T1 MRI signal were observed in muscle (FIGS. 1A and 1B), indicating that expression of the MLL-AF9 transgene is not sufficient to mediate changes in T1 MRI signal in other tissues and suggesting that this difference reflects changes in physiology that are specific to the hematologic system and/or the bone marrow in MLL-AF9 Tg mice. When normalized to muscle T1-signal intensity, bone marrow T1-weighted MRI signal intensity was approximately 70% greater in leukemic animals compared to healthy littermates (FIG. 1C). This inverse correlation is evident in a comparison of FIG. 1B and FIG. 1D. Thus, changes in bone marrow physiology in leukemic mice result in increased T1-weighted MRI signal-intensity and decreased T1-weighted relaxation time.

Example 2

Use of Contrast Agent in Assessing Bone Marrow Vasculature

Figure 2A:
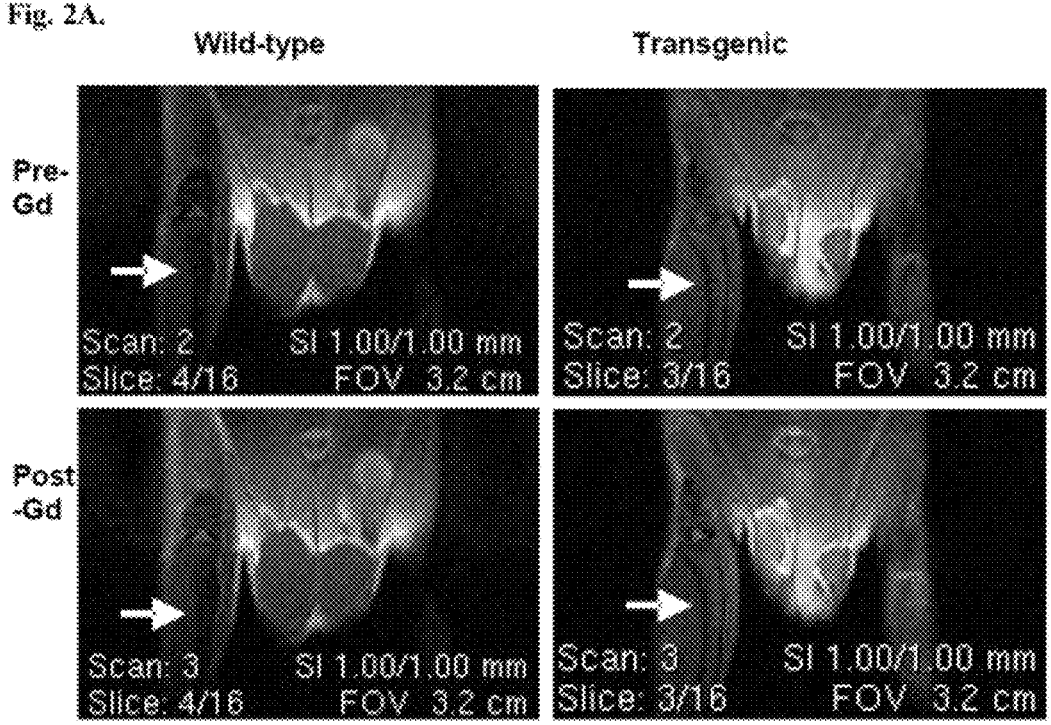
FIGS. 2A-2C depict enhancement of bone marrow T1-weighted MRI signal intensity following administration of gadodiamide contrast agent in leukemic MLL-AF9 Tg and WT mice and provide evidence that enhancement is not significantly different between mouse type. Abbreviations are as provided in FIGS. 1A-1C.
Figure 2B:
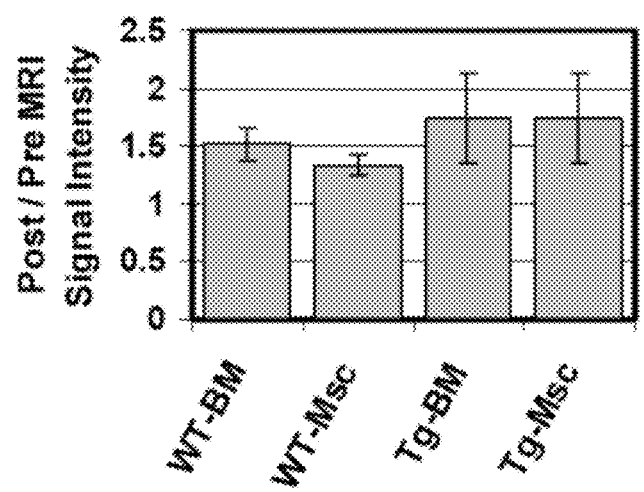
Figure 2C:
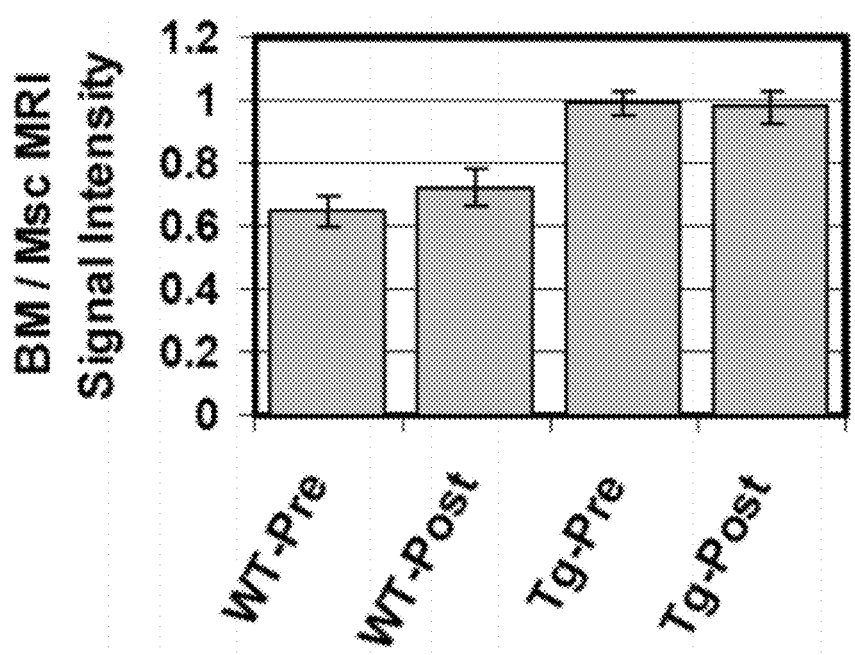

Upon injection of a gadolinium-based contrast agent, signal intensity was increased in both bone marrow and muscle in MLL-AF9 Tg mice and wild-type littermates. See FIGS. 2A and 2B. The ratios of signal intensity in bone marrow relative to muscle were not significantly different with and without contrast agent, as judged by the result depicted in FIG. 2C which is the ratio of bone marrow to muscle signal intensity for WT and Tg mice, before and after administration of contrast agent. Thus, changes in bone marrow physiology in leukemic mice do not affect signal enhancement by gadodiamide. Without wishing to be bound by theory, it is believed that if the difference in bone marrow MRI signal intensity in leukemic mice reflects changes in vascular density or vascular permeability then it would be expected that this difference would be more pronounced following injection of a contrast agent. Thus, it is believed that increased bone marrow MRI signal intensity does not reflect changes in the bone marrow vasculature.

Example 3

Effect of Angiogenesis on MRI Signal

Figure 3A:
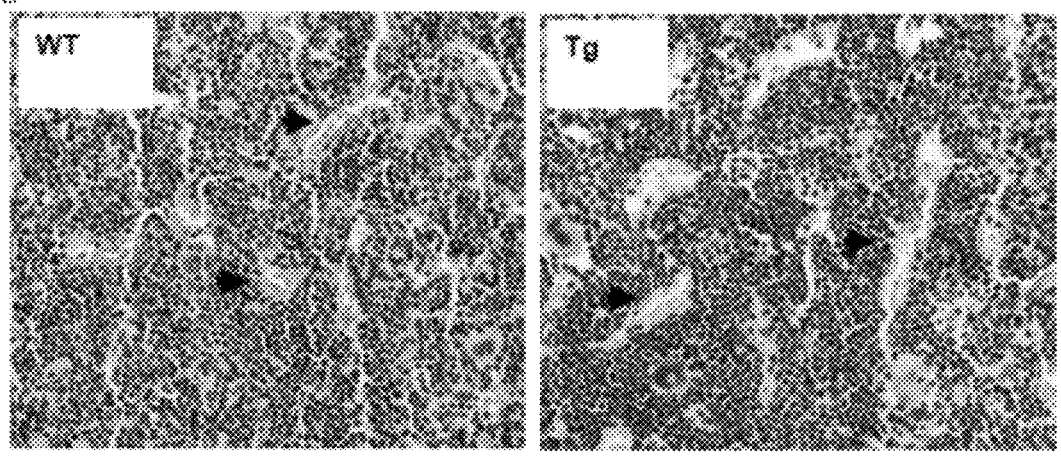
FIGS. 3A-3B provide evidence that leukemic MLL-AF9 Tg mice do not exhibit increased bone marrow microvessel density relative to WT mice. Abbreviations are as provided in FIGS. 1A-1C.
Figure 3B:
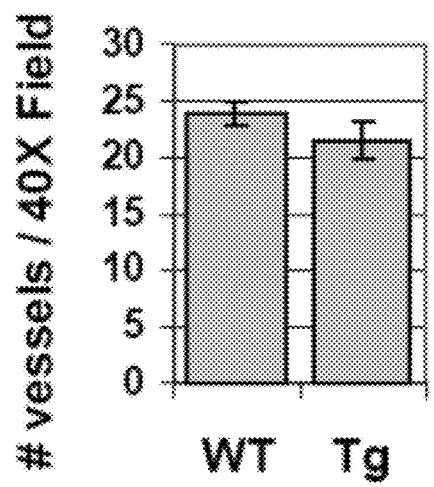

In order to more directly investigate the mechanism by which changes in bone marrow MRI signal intensity in leukemic mice are mediated, the density of microvessels in the bone marrow of leukemic mice and WT littermates was determined. For these experiments, femurs were collected from MLL-AF9 Tg mice with overt leukemia and WT littermates, fixed in paraformaldehyde, and decalcified. Sections were stained with hematoxylin and eosin and microvessel density was determined. No significant difference in bone-marrow microvessel density was observed in leukemic MLL-AF9 Tg mice relative to WT littermates (FIGS. 3A and 3B), indicating that differences in bone marrow MRI signal intensity do not reflect changes in angiogenesis.

Example 4

Bone Marrow Cell Density Studies

Figure 4A:
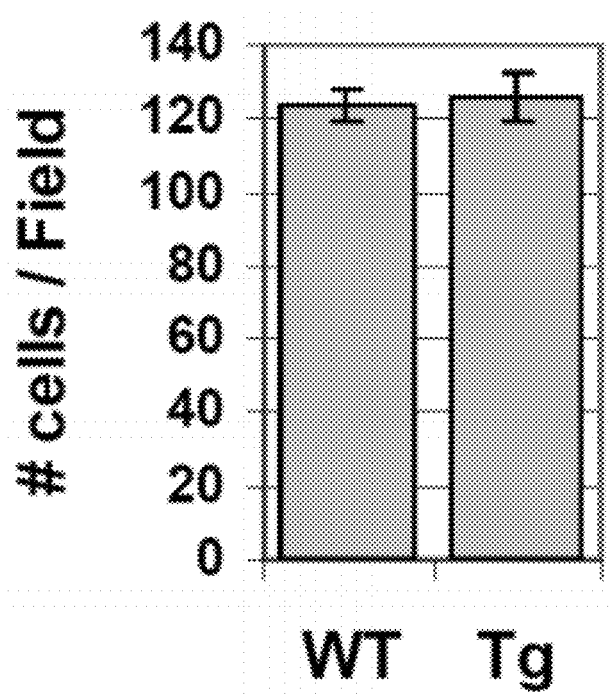
FIGS. 4A-4B provide evidence that increased bone marrow T1-weighted MRI signal intensity correlates with increased proliferation in the bone marrow and does not reflect an increase in bone marrow cell density. Abbreviations are as provided in FIGS. 1A-1C.
Figure 4B:
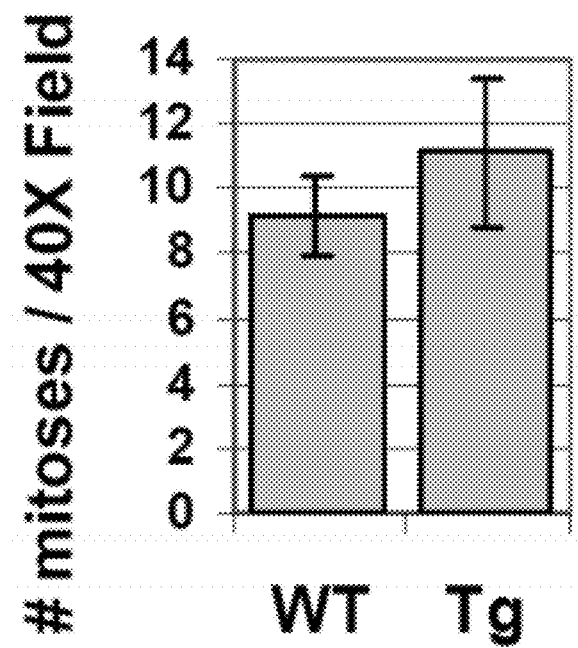

Investigation of bone marrow cell density resulted in no significant difference in bone marrow cell density observed in leukemic MLL-AF9 Tg and healthy mice (FIG. 4A). In contrast, changes in bone marrow MRI signal intensity were accompanied by an increase in the fraction of proliferating cells in the bone marrow of leukemic mice (FIG. 4B). MLL-AF9 Tg mice exhibit a preneoplastic myeloproliferative phenotype in their bone marrow as early as 6 days post-natal, but do not develop leukemia until a median age of 5 months (Dobson et al., 1999, Id.)

Example 5

Effect of Myeloproliferation or Transformation on MRI Signal Intensity

Figure 5A:
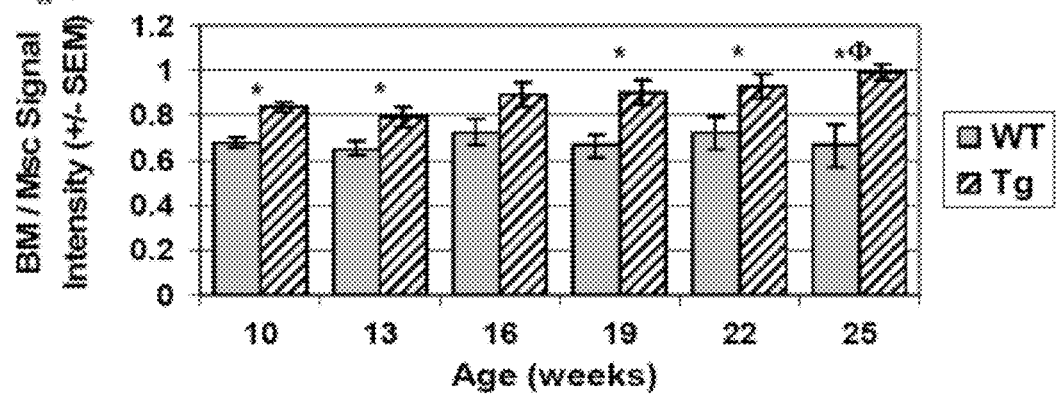
FIGS. 5A-5C depict evidence that increase bone marrow T1-weighted MRI signal intensity precedes development of leukemia in MLL-AF9 Tg mice. Abbreviations are as provided in FIGS. 1A-1C.
Figure 5B:
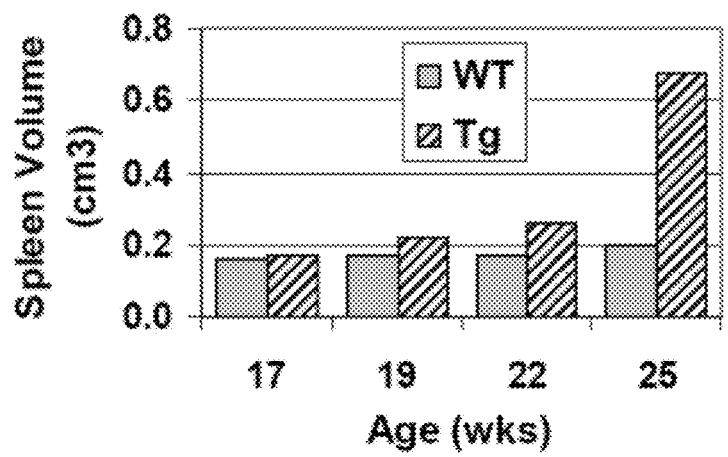
Figure 5C:
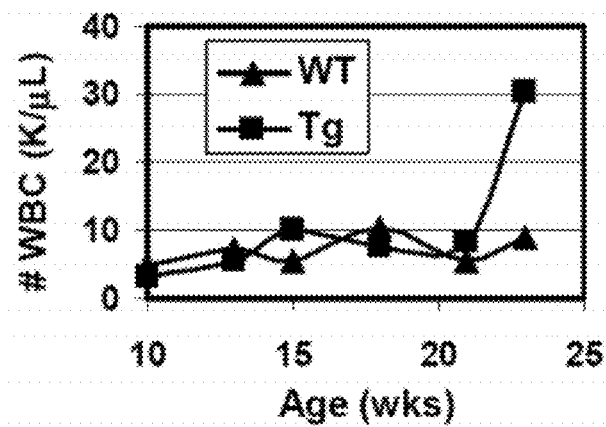

In order to determine whether changes in bone marrow MRI signal intensity reflect differences in myeloproliferation or require leukemic transformation, the MRI signal intensity in MLL-AF9 Tg mice was determined over time as the subject mice progressed from a pre-leukemic phenotype to development of overt leukemia. MLL-AF9 Tg mice exhibited a significant increase in bone marrow T1-weighted MRI signal intensity as early as 10 weeks of age (FIG. 5A). This increase was evident prior to development of leukemia, which was characterized by increased peripheral white blood cell count (>20K/µL) and/or a >2-fold increase in spleen volume and did not occur prior to 16 weeks of age in any of the subject animal used for these studies. See FIG. 5B and FIG. 5C. Although onset of leukemia was not required for changes in bone marrow MRI signal intensity, the magnitude of the increase in signal intensity increased over time and was significantly greater in mice with overt leukemia than in mice with pre-neoplastic disease (FIG. 5A), indicating that although leukemic transformation is not absolutely required for increased bone marrow MRI signal intensity, it is required for a maximal increase.

Example 6

Correlation of Metabolism with Bone Marrow MRI Signal Intensity

Figure 6A:
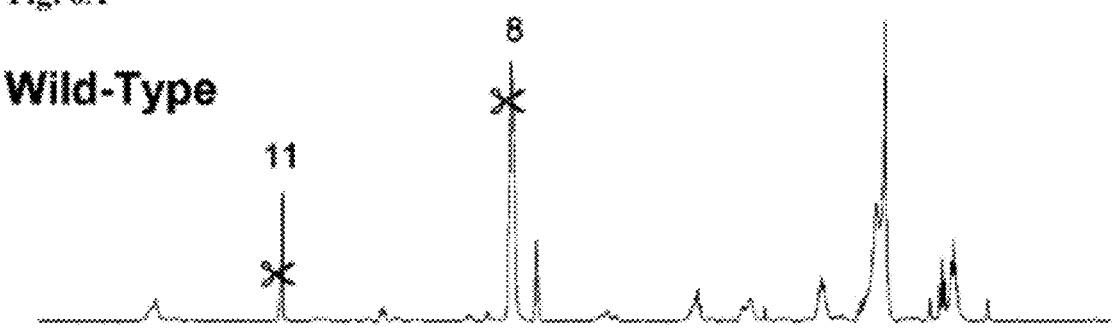
FIGS. 6A-6B depict high-resolution $^1$H-MR spectra of lipid extracts from wild-type mice and leukemic MLL-Af9 transgenic mice.
Figure 6B:
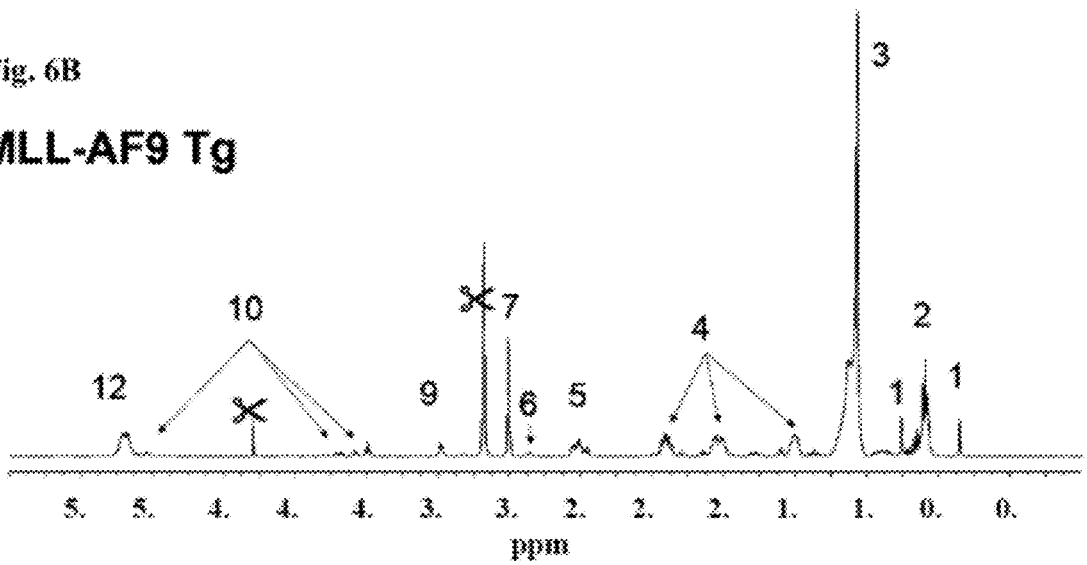

Changes in cell biology during development of cancers often include alterations in metabolic phenotype which can occur at a very early stage of tumorigenesis. (Spratlin et al., 2009, *Clin Cancer Res.* 15:431-440) We hypothesize that changes in bone marrow MRI signal intensity reflect differences in metabolism associated with leukemogenesis. To investigate this possibility, we used quantitative $^1$H-MRS and $^{31}$P-MRS to determine the absolute concentrations and/or ratios of metabolites related to lipid and glucose metabolism in leukemic and healthy bone marrow. Significant changes in glucose metabolism were observed: elevated glycolytic activity was evident as indicated by increased lactate and alanine levels (Table 1). Decreased concentrations of glutamine and glutamate were also observed in leukemic mice (Table 1), suggesting increased utilization of glutamine as an energy source (glutaminolysis) to compensate for disturbances in the mitochondrial Krebs cycle and to provide a carbon source for the increased macromolecular synthesis associated with highly proliferative tissues. (DeBerardinis et al., 2008, *Cell Metab.* 7:11-20) However, the most extensive changes in leukemic bone marrow were highly elevated levels of intracellular lipids and phospholipids (Table 1 and FIGS. 6A-6B). Leukemic mice exhibit significant increases in levels of glycerol-phospholipids, phosphatidylinositol (Ptdlns), phosphatidylcholine (PtdCho), phosphocholine (PCho), mono-unsaturated fatty acids (MUFAs), $(CH2)_n$, saturated lipids, and total lipids, and increased ratios of PCho/glycerophosphocholine (GPCho) and phosphate monoesters/phosphate diesters (PME/PDE) in bone marrow. In contrast, ratios of poly-unsaturated fatty acids (PUFA)/MUFA were decreased in leukemic bone marrow.

TABLE 1

Metabolite levels in bone marrow of leukemic MLL-AF9 transgenic mice and wild-type littermates.

| | Mean Concentration (µmol/g) | | |
|---|---|---|---|
| Metabolite | Tg | WT | p value |
| Lactate | 1.840 +/− 0.237 | 0.780 +/− 0.137 | 0.0020 |
| Alanine | 0.904 +/− 0.103 | 0.438 +/− 0.037 | 0.0008 |
| Glutamine | 0.430 +/− 0.031 | 0.653 +/− 0.063 | 0.0119 |
| Glutamate | 1.318 +/− 0.060 | 1.660 +/− 0.069 | 0.0035 |
| PCho | 1.150 +/− 0.131 | 0.460 +/− 0.107 | 0.0151 |
| MUFA | 4.779 +/− 0.388 | 2.316 +/− 0.145 | 0.0001 |
| Glycerol-Plipids | 2.218 +/− 0.245 | 1.497 +/− 0.078 | 0.0123 |
| Ptdlnositol | 0.406 +/− 0.035 | 0.198 +/− 0.029 | 0.0007 |
| PtdCho | 3.636 +/− 0.346 | 1.682 +/− 0.250 | 0.0007 |
| (CH2)n-Lipids (saturated) | 244.4 +/− 25.11 | 170.0 +/− 12.29 | 0.0176 |
| Total lipids | 48.49 +/− 3.08 | 36.17 +/− 3.014 | 0.0160 |
| [PCho/GPCho] | 6.937 +/− 0.640 | 1.058 +/− 0.259 | 0.0010 |
| [PME/PDE] | 5.299 +/− 0.145 | 1.259 +/− 0.166 | 0.0001 |
| [PUFA/MUFA] | 1.715 +/− 0.090 | 4.292 +/− 0.367 | 0.0001 |

Example 7

Bone Marrow Metabolism Studies

Increased bone marrow MRI signal intensity correlates with increased proliferation in leukemic MLL-AF9 Tg mice. Increased levels of choline-containing compounds (for example, choline, phosphocholine, and glycerophosphocholine) have also been associated with increased cell proliferation (reviewed in Glunde & Serkova, 2006, *Pharmacogenomics* 7:1109-1123). Taken together, these observations suggest that phospholipid and phospholipid-precursor levels are useful indicators of leukemia in the bone marrow. To determine whether changes in bone marrow lipid metabolite levels accompany changes in bone marrow MRI signal intensity, quantitative MRS was employed in conjunction with mass spectrometry/gas chromatography to quantitate the concentrations of phospholipids, phospholipid-precursors and additional cellular components as indicated in Tables 2A-2D following in bone marrow cells isolated from leukemic MLL-AF9 Tg mice and WT littermates. In Tables 2A-2D, where the number of samples is one, the SEM and p-value fields cannot be calculated and are blank.

TABLE 2A

Metabolite levels in bone marrow of leukemic MLL-AF9 transgenic mice and wild-type littermates.

| | Mean (µmol/g or µmol/g/4 hr) | | SEM | | n | | p value |
|---|---|---|---|---|---|---|---|
| Metabolite | Tg | WT | Tg | WT | Tg | WT | |
| Aromatic Acids | 10.457 | 10.672 | 0.614 | 1.037 | 6 | 7 | 0.8677 |
| Adenine | 0.765 | 0.907 | 0.073 | 0.101 | 6 | 7 | 0.2950 |
| Adenosine | 1.341 | 1.411 | 0.090 | 0.085 | 6 | 7 | 0.5869 |
| Nucleotides | 1.130 | 0.965 | 0.126 | 0.120 | 6 | 7 | 0.3648 |
| Myo-inositol | 0.990 | 1.230 | 0.070 | 0.025 | 6 | 7 | 0.0055 |
| Polyols | 12.236 | 11.371 | 1.610 | 1.257 | 6 | 7 | 0.6758 |
| Glycine | 1.241 | 1.082 | 0.256 | 0.135 | 6 | 7 | 0.5749 |
| Taurine | 3.353 | 3.874 | 0.268 | 0.252 | 6 | 7 | 0.1846 |
| PC + GPC + Cho | 1.682 | 1.852 | 0.162 | 0.167 | 6 | 7 | 0.4824 |
| Cr + PCr | 0.346 | 0.421 | 0.012 | 0.046 | 6 | 7 | 0.1731 |
| GSH | 0.795 | 0.832 | 0.045 | 0.037 | 6 | 7 | 0.5348 |
| Aspartate | 0.108 | 0.179 | 0.030 | 0.032 | 6 | 7 | 0.1374 |
| Total glutathione | 1.227 | 1.379 | 0.083 | 0.081 | 6 | 7 | 0.2188 |
| Glutamine | 0.430 | 0.653 | 0.031 | 0.063 | 6 | 7 | 0.0119 |
| Succinate | 0.261 | 0.292 | 0.050 | 0.026 | 6 | 7 | 0.5730 |

TABLE 2A-continued

Metabolite levels in bone marrow of leukemic MLL-AF9 transgenic mice and wild-type littermates.

| Metabolite | Mean (µmol/g or µmol/g/4 hr) | | SEM | | n | | p value |
|---|---|---|---|---|---|---|---|
| | Tg | WT | Tg | WT | Tg | WT | |
| Glutamate | 1.318 | 1.660 | 0.060 | 0.069 | 6 | 7 | 0.0035 |
| All CH3-Acetyl | 3.600 | 3.923 | 0.243 | 0.119 | 6 | 7 | 0.2370 |
| Acetate | 0.114 | 0.066 | 0.011 | 0.014 | 6 | 7 | 0.0261 |
| Lysine + Arginine | 0.286 | 0.231 | 0.036 | 0.025 | 6 | 7 | 0.2203 |
| Alanine | 0.904 | 0.438 | 0.103 | 0.037 | 6 | 7 | 0.0008 |
| Lactate | 1.840 | 0.780 | 0.237 | 0.137 | 6 | 7 | 0.0020 |
| Lactate* | 0.224 | 0.058 | 0.047 | 0.012 | 6 | 7 | 0.0034 |
| OH_butyrate | 0.000 | 0.000 | 0.000 | 0.000 | 6 | 7 | #DIV/0! |
| Val, Leu, Ile | 0.718 | 0.844 | 0.025 | 0.058 | 6 | 7 | 0.0883 |
| BM Weight [g] | 0.020 | 0.019 | 0.005 | 0.002 | 6 | 7 | 0.8580 |

Abbreviations: BM Weight: body mass weight

TABLE 2B

Metabolite levels in bone marrow of leukemic MLL-AF9 transgenic mice and wild-type littermates.

| Metabolite | Mean (µmol/g or µmol/g/4 hr) | | SEM | | n | | p value |
|---|---|---|---|---|---|---|---|
| | Tg | WT | Tg | WT | Tg | WT | |
| 13C-Glucose | 0.120 | 0.340 | | | 1 | 1 | #DIV/0! |
| 13C-TCA cycle | 0.120 | 0.230 | | | 1 | 1 | #DIV/0! |
| 13C-Glycolysis | 0.190 | 0.070 | | | 1 | 1 | #DIV/0! |
| [Glycolysis/Glc] | 1.583 | 0.206 | | | 1 | 1 | #DIV/0! |

Abbreviations: [Glycolysis/Glc]: ratio of $^{13}$C-Glycolysis to $^{13}$C-Glucose.

TABLE 2C

Metabolite levels in bone marrow of leukemic MLL-AF9 transgenic mice and wild-type littermates.

| Metabolite | Mean (µmol/g or µmol/g/4 hr) | | SEM | | n | | p value |
|---|---|---|---|---|---|---|---|
| | Tg | WT | Tg | WT | Tg | WT | |
| ATP | 0.820 | 0.870 | 0.146 | 0.121 | 3 | 3 | 0.8050 |
| ADP | 0.410 | 0.267 | 0.056 | 0.023 | 3 | 3 | 0.0765 |
| NAD+ | 0.307 | 0.380 | 0.103 | 0.025 | 3 | 3 | 0.5261 |
| UDPG | 0.260 | 0.247 | 0.045 | 0.018 | 3 | 3 | 0.7967 |
| Phosphocholine | 1.150 | 0.460 | 0.131 | 0.107 | 3 | 3 | 0.0151 |
| P-Ethanolamine | 1.720 | 0.910 | 0.442 | 0.081 | 3 | 3 | 0.1455 |
| GP-Choline | 0.193 | 0.557 | 0.049 | 0.168 | 3 | 3 | 0.1059 |
| GP-Ethanolamine | 0.230 | 0.467 | 0.006 | 0.094 | 3 | 3 | 0.0649 |
| Total PME | 2.870 | 1.367 | 0.544 | 0.175 | 3 | 3 | 0.0580 |
| Total PDE | 0.517 | 1.150 | 0.091 | 0.263 | 3 | 3 | 0.0849 |
| [ATP/ADP] | 2.122 | 3.246 | 0.521 | 0.198 | 3 | 3 | 0.1141 |
| [PC/GPC] | 6.937 | 1.058 | 0.640 | 0.259 | 3 | 3 | 0.0010 |
| [PME/PDE] | 5.299 | 1.259 | 0.145 | 0.166 | 3 | 3 | 0.0001 |

TABLE 2D

Metabolite levels in bone marrow of leukemic MLL-AF9 transgenic mice and wild-type littermates.

| Metabolite | Mean (µmol/g or µmol/g/4 hr) | | SEM | | n | | p value |
|---|---|---|---|---|---|---|---|
| | Tg | WT | Tg | WT | Tg | WT | |
| Sphingomyelin | 0.253 | 0.156 | 0.066 | 0.014 | 6 | 7 | 0.1474 |

TABLE 2D-continued

Metabolite levels in bone marrow of leukemic MLL-AF9 transgenic mice and wild-type littermates.

| Metabolite | Mean (µmol/g or µmol/g/4 hr) | | SEM | | n | | p value |
|---|---|---|---|---|---|---|---|
| | Tg | WT | Tg | WT | Tg | WT | |
| MUFA | 4.779 | 2.316 | 0.388 | 0.145 | 6 | 7 | 0.0001 |
| TAG | 0.984 | 0.780 | 0.141 | 0.047 | 6 | 7 | 0.1709 |
| Glycerol-Plipids | 2.218 | 1.497 | 0.245 | 0.078 | 6 | 7 | 0.0123 |
| PtdInositol | 0.406 | 0.198 | 0.035 | 0.029 | 6 | 7 | 0.0007 |
| PtdCholine | 3.636 | 1.682 | 0.346 | 0.250 | 6 | 7 | 0.0007 |
| Total Cholines | 3.539 | 3.487 | 0.091 | 0.161 | 6 | 7 | 0.7925 |
| PtdEthanolamine | 0.260 | 0.180 | 0.068 | 0.024 | 6 | 7 | 0.2580 |
| PUFA | 7.955 | 9.420 | 0.385 | 0.655 | 6 | 7 | 0.0926 |
| Fatty Acids | 24.321 | 21.558 | 2.201 | 1.009 | 6 | 7 | 0.2549 |
| (CH2)n-Lipids | 244.411 | 170.049 | 25.107 | 12.293 | 6 | 7 | 0.0176 |
| Total lipids | 48.488 | 36.174 | 3.083 | 3.014 | 6 | 7 | 0.0160 |
| Cholesterol | 1.996 | 2.035 | 0.141 | 0.072 | 6 | 7 | 0.7996 |
| [PUFA/MUFA] | 1.715 | 4.292 | 0.090 | 0.367 | 6 | 7 | 0.0001 |

Based on the data provided in Tables 2A-2D, leukemic MLL-AF9 Tg mice exhibit significant (p<0.05) decreases, relative to WT littermates, of the following cellular components: myo-inositol, glutamine, glutamate, branched aliphatic amino acids (Val, Leu, Ile), and the ratio of polyunsaturated to monounsaturated fatty acids ([PUFA/MUFA]). In contrast, significant (p<0.05) increases are observed for the following components: alanine, lactate, MUFA, glycerol-phospholipids, phosphatidylinositol and phosphatidylcholine.

Example 8

Spleen Metabolism Studies

Changes in spleen metabolite levels were determined by quantitative MRS in conjunction with mass spectrometry/gas chromatography to quantitate the concentrations of cellular components as indicated in Tables 3A-2D following in spleen cells isolated from leukemic MLL-AF9 Tg mice and WT littermates. In Tables 3A-2D, where the number of samples is one, the SEM and p-value fields cannot be calculated and are blank.

TABLE 3A

Metabolite levels in spleen of leukemic MLL-AF9 transgenic mice and wild-type littermates.

| Metabolite | Mean (µmol/g or µmol/g/4 hr) | | SEM | | n | | p value |
|---|---|---|---|---|---|---|---|
| | Tg | WT | Tg | WT | Tg | WT | |
| Aromatic Acids | 9.285 | 12.658 | 0.308 | 0.525 | 7 | 8 | 0.0001 |
| Adenine | 2.097 | 2.050 | 0.073 | 0.046 | 7 | 8 | 0.5860 |
| Adenosine | 2.020 | 1.910 | 0.025 | 0.074 | 7 | 8 | 0.2027 |
| Nucleotides | 2.066 | 1.701 | 0.035 | 0.096 | 7 | 8 | 0.0049 |
| Myo-inositol | 0.786 | 0.844 | 0.034 | 0.023 | 7 | 8 | 0.1733 |
| Polyols | 15.081 | 16.855 | 0.901 | 0.448 | 7 | 8 | 0.0895 |
| Glycine | 1.865 | 1.475 | 0.061 | 0.053 | 7 | 8 | 0.0003 |
| Taurine | 10.025 | 12.892 | 0.468 | 0.825 | 7 | 8 | 0.0123 |
| PC + GPC + Cho | 3.534 | 2.594 | 0.360 | 0.105 | 7 | 8 | 0.0196 |
| Cr + PCr | 0.446 | 0.652 | 0.075 | 0.036 | 7 | 8 | 0.0229 |
| GSH | 1.279 | 1.389 | 0.053 | 0.040 | 7 | 8 | 0.1144 |
| Aspartate | 1.183 | 1.204 | 0.046 | 0.071 | 7 | 8 | 0.8124 |

TABLE 3A-continued

Metabolite levels in spleen of leukemic MLL-AF9 transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| Total glutathione | 2.228 | 1.756 | 0.094 | 0.059 | 7 | 8 | 0.0008 |
| Glutamine | 0.367 | 0.438 | 0.017 | 0.024 | 7 | 8 | 0.0329 |
| Succinate | 0.699 | 0.434 | 0.047 | 0.028 | 7 | 8 | 0.0002 |
| Glutamate | 2.816 | 2.993 | 0.065 | 0.096 | 7 | 8 | 0.1618 |
| All CH2, CH3-Acetyl | 5.391 | 5.372 | 0.149 | 0.234 | 7 | 8 | 0.9477 |
| Acetate | 0.116 | 0.152 | 0.012 | 0.017 | 7 | 8 | 0.1248 |
| Lysine + Arginine | 0.335 | 0.718 | 0.026 | 0.053 | 7 | 8 | 0.0000 |
| Alanine | 0.914 | 0.629 | 0.033 | 0.034 | 7 | 8 | 0.0001 |
| Lactate | 2.913 | 1.695 | 0.250 | 0.082 | 7 | 8 | 0.0003 |
| Lactate* | 0.114 | 0.056 | 0.009 | 0.004 | 7 | 8 | 0.0000 |
| OH_butyrate | 0.174 | 0.128 | 0.020 | 0.006 | 7 | 8 | 0.0323 |
| Val, Leu, Ile | 1.429 | 1.538 | 0.046 | 0.071 | 7 | 8 | 0.2398 |
| Spleen Weight [g] | 0.599 | 0.089 | 0.123 | 0.011 | 7 | 8 | 0.0007 |

TABLE 3B

Metabolite levels in spleen of leukemic MLL-AF9 transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| 13C-Glucose | 0.280 | 0.337 | 0.021 | 0.024 | 7 | 6 | 0.1057 |
| 13C-TCA cycle | 0.501 | 0.617 | 0.048 | 0.029 | 7 | 6 | 0.0723 |
| 13C-Glycolysis | 0.351 | 0.198 | 0.046 | 0.051 | 7 | 6 | 0.0466 |
| [Glycolysis/Glc] | 1.147 | 0.527 | 0.148 | 0.093 | 7 | 6 | 0.0059 |

TABLE 3C

Metabolite levels in spleen of leukemic MLL-AF9 transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| ATP | 1.094 | 1.262 | 0.089 | 0.049 | 7 | 6 | 0.1456 |
| ADP | 0.664 | 0.653 | 0.030 | 0.078 | 7 | 6 | 0.8915 |
| NAD+ | 0.559 | 0.470 | 0.062 | 0.020 | 7 | 6 | 0.2318 |
| UDPG | 0.356 | 0.145 | 0.042 | 0.024 | 7 | 6 | 0.0017 |
| Phosphocholine | 1.254 | 0.588 | 0.327 | 0.022 | 7 | 6 | 0.0885 |
| P-Ethanolamine | 2.866 | 2.907 | 0.207 | 0.229 | 7 | 6 | 0.8966 |
| GP-Choline | 0.476 | 0.572 | 0.061 | 0.053 | 7 | 6 | 0.2701 |
| GP-Ethanolamine | 0.153 | 0.215 | 0.019 | 0.016 | 7 | 6 | 0.0348 |
| Total PME | 4.119 | 3.495 | 0.509 | 0.231 | 7 | 6 | 0.3153 |
| Total PDE | 0.721 | 0.892 | 0.124 | 0.114 | 7 | 6 | 0.3412 |
| [ATP/ADP] | 1.674 | 2.100 | 0.172 | 0.304 | 7 | 6 | 0.2322 |
| [PC/GPC] | 3.857 | 1.067 | 1.632 | 0.097 | 7 | 6 | 0.1445 |
| [PME/PDE] | 7.991 | 4.085 | 2.478 | 0.328 | 7 | 6 | 0.1773 |

TABLE 3D

Metabolite levels in spleen of leukemic MLL-AF9 transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| Sphingomyelin | 0.509 | 0.521 | 0.042 | 0.068 | 7 | 8 | 0.8824 |
| MUFA | 12.608 | 10.490 | 0.489 | 0.818 | 7 | 8 | 0.0519 |
| TAG | 5.060 | 4.767 | 0.711 | 0.587 | 7 | 8 | 0.7537 |
| Glycerol-Plipids | 7.767 | 6.156 | 0.618 | 0.509 | 7 | 8 | 0.0632 |
| PtdInositol | 1.335 | 1.027 | 0.861 | 0.534 | 7 | 8 | 0.7597 |
| PtdCholine | 5.337 | 4.329 | 0.886 | 0.510 | 7 | 8 | 0.3271 |
| Total Cholines | 8.339 | 7.225 | 0.490 | 0.325 | 7 | 8 | 0.0744 |
| PtdEthanol-amine | 1.748 | 1.929 | 0.124 | 0.310 | 7 | 8 | 0.6144 |
| PUFA | 32.061 | 31.708 | 1.567 | 0.638 | 7 | 8 | 0.8297 |
| Fatty Acids | 44.275 | 36.944 | 3.787 | 2.179 | 7 | 8 | 0.1067 |
| (CH2)n-Lipids | 446.207 | 390.730 | 23.245 | 9.585 | 7 | 8 | 0.0375 |
| Total lipids | 92.836 | 70.907 | 4.038 | 7.708 | 7 | 8 | 0.0314 |
| Cholesterol | 5.210 | 4.758 | 0.609 | 0.188 | 7 | 8 | 0.4661 |
| [PUFA/MUFA] | 2.549 | 3.159 | 0.090 | 0.262 | 7 | 8 | 0.0575 |

Example 9

Blood Metabolism Studies

Changes in blood metabolite levels were determined by quantitative MRS in conjunction with mass spectrometry/gas chromatography to quantitate the concentrations of cellular components as indicated in Tables 4A-2D following in blood isolated from leukemic MLL-AF9 Tg mice and WT littermates. In Tables 4A-2D, where the number of samples is one, the SEM and p-value fields cannot be calculated and are blank.

TABLE 4A

Metabolite levels in blood of leukemic MLL-AF9 transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| Aromatic Acids | 2.410 | 2.611 | 0.227 | 0.827 | 7 | 8 | 0.8297 |
| Adenine | 0.299 | 0.304 | 0.041 | 0.027 | 7 | 8 | 0.9235 |
| Adenosine | 0.096 | 0.070 | 0.012 | 0.006 | 7 | 8 | 0.0632 |
| Glucose (total) | 2.613 | 3.785 | 0.277 | 0.282 | 7 | 8 | 0.0114 |
| Creatinine | 0.028 | 0.023 | 0.003 | 0.006 | 7 | 8 | 0.5315 |
| Inositol | 3.569 | 3.505 | 0.289 | 0.136 | 7 | 8 | 0.8362 |
| Polyols | 16.436 | 17.713 | 1.149 | 1.191 | 7 | 8 | 0.4571 |
| TMAO | 0.152 | 0.092 | 0.039 | 0.016 | 7 | 8 | 0.1551 |
| PC + GPC | 0.149 | 0.157 | 0.027 | 0.021 | 7 | 8 | 0.8242 |
| Free Choline | 0.024 | 0.025 | 0.001 | 0.001 | 7 | 8 | 0.8096 |
| PC + GPC + Cho | 0.169 | 0.181 | 0.027 | 0.020 | 7 | 8 | 0.8135 |
| Tyrosine | 0.144 | 0.154 | 0.010 | 0.014 | 7 | 8 | 0.5447 |
| Creatine + Crn | 0.116 | 0.129 | 0.019 | 0.012 | 7 | 8 | 0.5563 |
| GSH | 0.432 | 0.460 | 0.082 | 0.032 | 7 | 8 | 0.7426 |
| Aspartate | 0.030 | 0.034 | 0.005 | 0.008 | 7 | 8 | 0.7025 |
| Citrate | 0.103 | 0.208 | 0.023 | 0.015 | 7 | 8 | 0.0017 |
| total Glutathione | 0.567 | 0.559 | 0.108 | 0.032 | 7 | 8 | 0.9445 |
| Glutamine | 0.329 | 0.319 | 0.068 | 0.038 | 7 | 8 | 0.8949 |
| Succinate | 0.122 | 0.068 | 0.010 | 0.007 | 7 | 8 | 0.0006 |
| Glutamate | 0.314 | 0.393 | 0.027 | 0.043 | 7 | 8 | 0.1567 |
| Acetyl-CH3 | 1.461 | 1.348 | 0.087 | 0.067 | 7 | 8 | 0.3179 |
| Acetate | 0.088 | 0.095 | 0.016 | 0.019 | 7 | 8 | 0.7713 |
| Lysine + Arginine | 0.226 | 0.226 | 0.011 | 0.044 | 7 | 8 | 0.9989 |
| Alanine | 0.267 | 0.214 | 0.065 | 0.019 | 7 | 8 | 0.4172 |
| Lactate (total) | 2.535 | 1.850 | 0.214 | 0.185 | 7 | 8 | 0.0301 |

TABLE 4A-continued

Metabolite levels in blood of leukemic MLL-AF9
transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| 13C-Lactate | 0.260 | 0.154 | 0.034 | 0.011 | 7 | 8 | 0.0087 |
| Val, Leu, Ile | 0.963 | 1.213 | 0.077 | 0.145 | 7 | 8 | 0.1684 |

TABLE 4B

Metabolite levels in blood of leukemic MLL-AF9
transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| 13C-Glucose | 0.652 | 0.922 | 0.046 | 0.096 | 3 | 4 | 0.0740 |
| 13C-Glycolysis | 0.338 | 0.196 | 0.111 | 0.024 | 3 | 4 | 0.2031 |
| [Glycolysis/Glc] | 0.551 | 0.213 | 0.223 | 0.017 | 3 | 4 | 0.1316 |
| [PC/GPC] | 1.720 | 1.020 | | | 1 | 1 | |

TABLE 4C

Metabolite levels in blood of leukemic MLL-AF9
transgenic mice and wild-type littermates.

| Metabolite | Mean (μmol/g or μmol/g/4 hr) | | SEM | | n | | p value |
|---|---|---|---|---|---|---|---|
| | Tg | WT | Tg | WT | Tg | WT | |
| Sphingomyelin | 0.147 | 0.110 | 0.020 | 0.014 | 7 | 8 | 0.1451 |
| MUFA | 2.514 | 1.830 | 0.255 | 0.140 | 7 | 8 | 0.0300 |
| TAG | 1.159 | 0.590 | 0.322 | 0.043 | 7 | 8 | 0.0827 |
| Glycerol-Plipids | 1.946 | 1.022 | 0.278 | 0.119 | 7 | 8 | 0.0070 |
| PtdInositol | 0.144 | 0.097 | 0.022 | 0.004 | 7 | 8 | 0.0416 |
| PtdCholine | 1.339 | 0.866 | 0.126 | 0.033 | 7 | 8 | 0.0019 |
| Total Cholines | 1.689 | 1.383 | 0.104 | 0.085 | 7 | 8 | 0.0375 |
| PtdEthanolamine | 0.183 | 0.179 | 0.018 | 0.014 | 7 | 8 | 0.8637 |
| PUFA | 5.334 | 3.722 | 0.405 | 0.292 | 7 | 8 | 0.0058 |
| Fatty Acids | 6.862 | 5.118 | 0.382 | 0.301 | 7 | 8 | 0.0031 |
| (CH2)n-Lipids | 65.786 | 46.123 | 5.850 | 1.715 | 7 | 8 | 0.0045 |
| Total lipids | 21.198 | 15.632 | 1.893 | 0.608 | 7 | 8 | 0.0110 |
| Cholesterol | 2.098 | 1.450 | 0.194 | 0.067 | 7 | 8 | 0.0053 |
| [PUFA/MUFA] | 2.289 | 2.132 | 0.241 | 0.159 | 7 | 8 | 0.5868 |

Discussion

The present results demonstrates a statistically significant increase in T1-weighted MRI signal intensity that correlates with decreased T1-weighted relaxation time in the bone marrow of MLL-AF9 Tg mice relative to WT littermates. This is the first report describing high-resolution MR imaging of bone marrow in mice. These data therefore demonstrate the feasibility of this approach. MLL-AF9 Tg mice do not exhibit significant differences in bone marrow microvessel density. Furthermore, MRI signal intensity enhancement following injection of a gadolinium-based contrast agent was similar in WT and leukemic mice. With the data taken together, it is believed that changes in MRI signal intensity in leukemic mice do not reflect differences in vasculature. Similarly, changes in MRI signal intensity do not reflect differences in bone marrow cell density in leukemic MLL-AF9 Tg mice. In contrast, a significant increase in the fraction of proliferating cells was observed in the bone marrow of MLL-AF9 Tg mice. In addition, increased bone marrow MRI signal intensity was evident in MLL-AF9 Tg mice as early as 10 weeks of age, prior to the onset of overt leukemia and coincident with a myeloproliferative phenotype that occurs as early as 6 days of age in these animals. Without wishing to be bound by theory, it is believed that changes in MRI signal intensity occur as a result of increased cell proliferation. Consistent with this idea, increased MRI signal intensity is accompanied by increased lipogenesis and lipid precursor levels, which have been associated with increased proliferation in both cancerous and non-cancerous tissues. Thus, changes in T1-weighted MRI signal intensity and/or lipid precursor and metabolite levels are useful indicators of changes in proliferation and, by extension, therapeutic efficacy.

Differences in T1-weighted MRI signal intensity and relaxation time in the bone marrow of patients with acute (overt) leukemia relative to non-leukemic patients have been described See for example Moulopoulos & Dimopoulos, 1997, *Blood* 90:2127-2147. However, in contrast to what is observed in mice and as disclosed herein, MRI signal intensities are decreased and T1 relaxation times are increased in the bone marrow of patients with leukemia. Without wishing to be bound by theory, this may reflect differences in normal bone marrow biology in mice and humans. For example, in humans decreased T1-weighted MRI signal intensity correlates with increased bone marrow cellularity and blast infiltration and is thought to result from replacement of fatty marrow, which has a relatively high MRI signal intensity, with leukemic blasts. However, mice normal bone marrow is 95-100% cellular and therefore has a lower fat content than in humans and a correspondingly lower MRI signal intensity. In addition, there is no significant difference in cell density in the bone marrow of leukemic MLL-AF9 Tg mice and healthy littermates.

Thus, without wishing to be bound by theory, it is believed that unlike in humans, in the murine model described herein, leukemogenesis does not induce significant changes in the composition of the marrow which allows for detection of more subtle changes in MRI signal intensity that reflect hyperproliferation. In contrast, in humans increased signal intensity as a result of increased proliferation is offset by the decrease in signal intensity that occurs as a result of decreased fat in the marrow. Consistent with this idea, in patients who have achieved remission, where the marrow has returned to its normal fatty composition, bone marrow MRI signal intensity is increased to normal levels. See for example Gerard et al., 1992, *Radiology* 183:39-46; Jensen et al., 1990, *Acta Radiol.* 31:361-369. However, patients with leukemia do exhibit a transient decrease in T1-weighted MRI signal intensity upon initiation of treatment with effective therapeutic regimens (Gerard et al., 1992, Id.), which, without wishing to be bound by theory, is believed to reflect decreased cell proliferation as a result of treatment. Without further wishing to be bound by theory, it is believed that changes in bone marrow T1-weighted MRI signal intensity indicate changes in cell proliferation which are in turn useful for early assessment of disease and therapeutic efficacy in humans. It is further believed that in the mouse model of leukemia described herein, bone marrow composition is normal, but proliferation is not. Accordingly, this model recapitulates the changes in bone marrow biology that contribute to decreases in MRI signal intensity during the early phase of therapeutic response in humans in the absence of changes that contribute to later increases in MRI signal intensity and, as such, is well-suited for studies investigating the early effects of therapeutic agents, and indeed the diagnosis of leukemia.

Changes in phospholipid metabolism are characteristic of leukemias and other tumors. For example, phosphocholine (PCho) is the major precursor for membrane synthesis, and PCho levels correlate with cell proliferation in a variety of cancerous and non-cancerous tissues (Glunde & Serkova, 2006, Id.) and are increased in all rapidly proliferating tumor cells, including leukemia (Gottschalk et al., 2004, *Clin Cancer Res* 10:6661-6668). Moreover, in leukemia cell lines, changes in lipid metabolite levels indicate response to both traditional cytotoxic therapies and modern molecularly-targeted agents. For example, in acute lymphoblastic leukemia (ALL) cell lines, decreased PCho+PEth and total PME levels are associated with sensitivity to dexamethasone (Adebodun and Post, 1994, *J Cell Physiol* 158:180-186). In BCR-Abl+ chronic lymphoblastic leukemia (CLL) cell lines, treatment with imatinib mesylate results in decreased levels of PtdCho, PCho, and total PMEs and a corresponding decrease in cell proliferation (Gottschalk et al., 2004, *Clin Cancer Res* 10:6661-6668). In contrast, imatinib-resistance is associated with higher levels of PtdCho. In the model described herein, leukemic bone marrow has increased levels of PCho, PEth, and PtdCho. Thus, changes in lipid metabolism in the bone marrow of leukemic MLL-AF9 Tg mice accurately reflect differences in lipid metabolism that are observed in human leukemia cell lines and/or patient samples and can be used as indicators of therapeutic efficacy.

Without wishing to be bound by theory, it is believed that increased levels of phospholipids (PtdIns, PtdCho, glycerol-phospholipids) and phospholipid-precursors (PCho, PEth, PMEs, PCho/GPC, MUFAs, and $(CH_2)_n$-lipids) in bone marrow from leukemic mice result from increased flux through lipid biosynthetic pathways and/or decreased lipid breakdown. It is further believed that these changes allow for increased macromolecular and membrane synthesis, thereby supporting the hyperproliferative phenotype of tumor cells. For example, increased MUFA levels are associated with progression toward transformation in rat hepatocyte nodules, and changes in phosphatidylinositol (PtdIns) and fatty acid levels are known to regulate signal transduction pathways involved in oncogenesis, apoptosis, and/or cell cycle regulation. See for example Steelman et al., 2008, *Leukemia* 22:686-707. Thus, observed changes in lipid metabolite levels are believe to indicate mechanisms of leukemogenesis that are physiologically relevant in vivo. Similarly, leukemic MLL-AF9 Tg bone marrow exhibited statistically significant decreases in the levels of PDEs, including GPC. Increased GPC levels are associated with breakdown of cell membranes in response to apoptotic stimuli in cancers and other cell types (Evelhoch et al., 2000, *Neoplasia* 2:152-165). In CLL cell lines, treatment with imatinib at a concentration sufficient to induce apoptosis results in increased levels of PDEs and GPC (Gottschalk et al., 2004, Id.). Thus, it is believed that leukemia cells in the bone marrow of MLL-AF9 Tg mice are resistant to apoptosis relative to normal bone marrow cells. Moreover, without wishing to be bound by theory, it is believed that because they are biochemical markers of apoptosis, changes in bone marrow PDE and GPC levels are preferred as early indicators of efficacy in response to treatment with traditional cytotoxic agents.

The experiments described here identify magnetic resonance markers in bone marrow, including T1-weighted MRI signal intensity and absolute levels of selected lipid metabolites that correlate with cell proliferation and/or leukemogenesis in an animal model of acute leukemia. These markers are useful as indicators of disease status and/or therapeutic efficacy. Both MRI signal intensity and lipid metabolite levels can be measured using non-invasive methods in humans and are therefore particularly attractive for assessment of bone marrow disease. Moreover, because these changes reflect alterations in leukemia cell biology and do not appear to require changes in cell density or cell number, they may be particularly useful as early indicators of therapeutic efficacy or disease burden. Without wishing to be bound by theory, it is believed that changes in lipid metabolism also have prognostic value and/or implicate novel targets for development of new therapies and new methods of diagnosis.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, any group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety and for all purposes. Definitions that are contained in text incorporated by reference are excluded to the extent that they contradict definitions described herein.

While preferred embodiments have been illustrated and described, it should be understood that changes and modifications can be made therein in accordance with ordinary skill in the art without departing from the invention in its broader aspects as defined in the following claims.

What is claimed is:

1. A method of detecting a plurality of endogenous biomolecules in a tissue of a subject that has or is suspected of having leukemia, said method comprising:
   detecting an elevated level of said plurality of endogenous biomolecules relative to a standard control using a magnetic resonance apparatus, wherein said plurality of endogenous molecules comprises monounsaturated fatty acids, total lipids and an additional endogenous biomolecule selected from the group consisting of phosphatidylinositol, phosphocholine and lactate, wherein a statistically elevated level of said plurality of endogenous biomolecules is indicative of said subject having leukemia.

2. The method of claim 1, wherein said detecting said elevated level of said plurality of endogenous marker biomolecules in said tissue is performed at a first time point, said method further comprising, prior to said first time point, detecting the level of said plurality of said endogenous marker biomolecules in said tissue at a control time point, wherein the levels of said endogenous marker biomolecules in said tissue at said control time point is said standard control.

3. The method of claim 1, wherein said standard control is a metabolite present at approximately the same levels in a population of said subjects, or said standard control is approximately the average level of said endogenous marker biomolecule present in a population of said subjects.

4. The method of claim 1, wherein said tissue is blood tissue, spleen tissue, or bone marrow tissue.

5. The method of claim 1, wherein said tissue is blood tissue.

6. The method of claim 1, wherein said tissue is spleen tissue.

7. The method of claim 1, wherein said tissue is bone marrow.

8. The method of claim 1, wherein said detecting said elevated level of said plurality of endogenous marker biomolecules further comprises detecting a level of at least 2, 3, 4, 5, 6, 7, 8, 9, or 10 of endogenous marker biomolecules selected from the group consisting of nucleotides, polyols, glycine, glycerophosphocholine, choline, creatine, phosphocreatine, succinate, alanine, hydroxybutyrate, glycerol phospholipids, total cholines, $(CH_2)_n$-lipids, acetate, adenosine diphosphate, phosphoethanolamine, phosphomonoesters, fatty acids, cholesterol, and adenosine.

9. A method of detecting a plurality of endogenous biomolecules in a tissue of a subject undergoing leukemia therapy, said method comprising:

detecting an elevated level of said plurality of endogenous biomolecules relative to a standard control using a magnetic resonance apparatus, wherein said plurality of endogenous molecules comprises monounsaturated fatty acids, total lipids and an additional endogenous biomolecule selected from the group consisting of phosphatidylinositol, phosphocholine and lactate, wherein a statistically elevated level of said plurality of endogenous biomolecules is indicative of said subject having leukemia.

10. The method of claim 9, further comprising continuing administration of said leukemia therapy to said subject.

* * * * *